US011564596B2

(12) United States Patent
Gifford, III et al.

(10) Patent No.: US 11,564,596 B2
(45) Date of Patent: Jan. 31, 2023

(54) SYSTEMS AND METHODS FOR PATIENT FLUID MANAGEMENT

(71) Applicant: Foundry Innovation & Research 1, Ltd., Dublin (IE)

(72) Inventors: Hanson S. Gifford, III, Woodside, CA (US); Mark E. Deem, Portola Valley, CA (US); Conor M. Hanley, Dublin (IE); Fiachra M. Sweeney, Dublin (IE); Jeffry J. Grainger, Portola Valley, CA (US); John R. Britton, Dublin (IE); Annette Kent, Dublin (IE)

(73) Assignee: Foundry Innovation & Research 1, Ltd., Dublin (IE)

( * ) Notice: Subject to any disclaimer, the term of this patent is extended or adjusted under 35 U.S.C. 154(b) by 1002 days.

(21) Appl. No.: 16/271,798

(22) Filed: Feb. 9, 2019

(65) Prior Publication Data

US 2019/0167188 A1 Jun. 6, 2019

Related U.S. Application Data

(63) Continuation of application No. PCT/US2017/046204, filed on Aug. 10, 2017.
(Continued)

(51) Int. Cl.
*A61B 5/107* (2006.01)
*A61B 5/00* (2006.01)
(Continued)

(52) U.S. Cl.
CPC .......... *A61B 5/1076* (2013.01); *A61B 5/0205* (2013.01); *A61B 5/076* (2013.01);
(Continued)

(58) Field of Classification Search
CPC ... A61B 5/0265; A61B 5/0295; A61B 5/1076; A61B 5/4875; A61B 8/0891; A61B 8/5223
See application file for complete search history.

(56) References Cited

U.S. PATENT DOCUMENTS

| 3,568,661 A | 3/1971 | Franklin |
| 4,142,412 A | 3/1979 | McLeod |

(Continued)

FOREIGN PATENT DOCUMENTS

| DE | 102005035022 A1 | 11/2006 |
| EP | 0399059 A1 | 5/1989 |

(Continued)

OTHER PUBLICATIONS

International Search Report and Written Opinion dated Mar. 3, 2020, in connection with PCT/US2019/066589 filed Dec. 16, 2019.
(Continued)

*Primary Examiner* — Daniel L Cerioni
*Assistant Examiner* — Raymond P Dulman
(74) *Attorney, Agent, or Firm* — Downs Rachlin Martin PLLC

(57) ABSTRACT

Systems and methods are disclosed that provide for regular, periodic or continuous monitoring of fluid volume based on direct measurement of an inferior vena cava (IVC) physical dimension using a wireless measurement sensor implanted in the IVC. By basing diagnostic decisions and treatments on changes in an IVC physical dimension, information on patient fluid state is available across the entire euvolemic range of fluid states, thus providing earlier warning of hypervolemia or hypovolemia and enabling the modulation of patient treatments to permit more stable long-term fluid management.

9 Claims, 14 Drawing Sheets

Related U.S. Application Data

(60) Provisional application No. 62/534,329, filed on Jul. 19, 2017, provisional application No. 62/427,631, filed on Nov. 29, 2016, provisional application No. 62/373,436, filed on Aug. 11, 2016.

(51) Int. Cl.
  *A61B 8/08* (2006.01)
  *A61B 8/12* (2006.01)
  *A61B 5/0205* (2006.01)
  *A61B 5/07* (2006.01)
  *A61B 8/00* (2006.01)
  A61B 5/024 (2006.01)
  A61B 5/021 (2006.01)
  A61B 5/0215 (2006.01)

(52) U.S. Cl.
  CPC .......... *A61B 5/4839* (2013.01); *A61B 5/4875* (2013.01); *A61B 5/6876* (2013.01); *A61B 5/746* (2013.01); *A61B 8/0891* (2013.01); *A61B 8/12* (2013.01); *A61B 8/5223* (2013.01); *A61B 8/5292* (2013.01); *A61B 8/56* (2013.01); *A61B 5/021* (2013.01); *A61B 5/024* (2013.01); *A61B 5/0215* (2013.01); *A61B 5/6882* (2013.01); *A61B 8/4472* (2013.01)

(56) References Cited

U.S. PATENT DOCUMENTS

| | | |
|---|---|---|
| 4,638,252 A | 1/1987 | Bradshaw |
| RE32,361 E | 2/1987 | Duggan |
| 4,733,669 A | 3/1988 | Segal |
| 4,926,875 A | 5/1990 | Rabinovitz et al. |
| 4,947,852 A | 8/1990 | Nassi et al. |
| 5,127,404 A | 7/1992 | Wyborny et al. |
| 5,205,292 A | 4/1993 | Czar et al. |
| 5,316,001 A | 5/1994 | Ferek-Petric et al. |
| 5,339,816 A | 8/1994 | Akamatsu et al. |
| 5,495,852 A | 3/1996 | Stadler et al. |
| 5,630,836 A | 5/1997 | Prem et al. |
| 5,752,522 A | 5/1998 | Murphy |
| 5,872,520 A | 2/1999 | Siefert et al. |
| 5,902,308 A | 5/1999 | Murphy |
| 5,967,986 A | 10/1999 | Cimochowski |
| 6,010,511 A | 1/2000 | Murphy |
| 6,012,457 A | 1/2000 | Lesh |
| 6,015,386 A | 1/2000 | Kensey et al. |
| 6,015,387 A | 1/2000 | Schwartz et al. |
| 6,025,725 A | 2/2000 | Gershenfeld et al. |
| 6,039,701 A | 3/2000 | Sliwa et al. |
| 6,053,873 A | 4/2000 | Govari et al. |
| 6,111,520 A | 8/2000 | Allen et al. |
| 6,115,633 A | 9/2000 | Lang et al. |
| 6,115,636 A | 9/2000 | Ryan |
| 6,164,283 A | 12/2000 | Lesh |
| 6,206,835 B1 | 3/2001 | Spillman, Jr. et al. |
| 6,231,516 B1 | 5/2001 | Keilman et al. |
| 6,261,233 B1 | 7/2001 | Kantorovich |
| 6,278,379 B1 | 8/2001 | Allen et al. |
| 6,287,253 B1 | 9/2001 | Ortega et al. |
| 6,325,762 B1 | 12/2001 | Tjin |
| 6,339,816 B1 | 1/2002 | Bausch |
| 6,354,999 B1 | 3/2002 | Dgany et al. |
| 6,398,734 B1 | 6/2002 | Cimochowski et al. |
| 6,434,411 B1 | 8/2002 | Duret |
| 6,503,202 B1 | 1/2003 | Hossack et al. |
| 6,574,510 B2 | 6/2003 | Von Arx et al. |
| 6,673,020 B2 | 1/2004 | Okada et al. |
| 6,699,186 B1 | 3/2004 | Wolinsky et al. |
| 6,738,671 B2 | 5/2004 | Christophersom et al. |
| 6,776,763 B2 | 8/2004 | Nix |
| 6,802,811 B1 | 10/2004 | Slepian |
| 6,855,115 B2 | 2/2005 | Fonseca et al. |
| 6,895,265 B2 | 5/2005 | Silver |
| 6,926,670 B2 | 8/2005 | Rich et al. |
| 6,972,553 B2 | 12/2005 | Petrovich et al. |
| 7,065,409 B2 | 6/2006 | Mazar |
| 7,077,812 B2 | 7/2006 | Naghavi |
| 7,082,330 B2 | 7/2006 | Stadler et al. |
| 7,147,604 B1 | 12/2006 | Mien et al. |
| 7,149,587 B2 | 12/2006 | Wardle et al. |
| 7,191,013 B1 | 3/2007 | Miranda et al. |
| 7,225,032 B2 | 5/2007 | Schmeling et al. |
| 7,233,821 B2 | 6/2007 | Hettrick |
| 7,236,821 B2 | 6/2007 | Cates et al. |
| 7,245,117 B1 | 7/2007 | Joy |
| 7,284,442 B2 | 10/2007 | Fleischman et al. |
| 7,367,984 B2 | 5/2008 | Kulcinski et al. |
| 7,423,496 B2 | 9/2008 | Scheuermann |
| 7,432,723 B2 | 10/2008 | Ellis |
| 7,439,723 B2 | 10/2008 | Allen |
| 7,444,878 B1 | 11/2008 | Pepples |
| 7,452,334 B2 | 11/2008 | Gianchandani et al. |
| 7,454,244 B2 | 11/2008 | Kassab et al. |
| 7,466,120 B2 | 12/2008 | Miller |
| 7,479,112 B2 | 1/2009 | Sweeney et al. |
| 7,481,771 B2 | 1/2009 | Fonseca |
| 7,492,144 B2 | 2/2009 | Powers et al. |
| 7,498,799 B2 | 3/2009 | Allen |
| 7,550,978 B2 | 6/2009 | Joy |
| 7,574,792 B2 | 8/2009 | O'Brien |
| 7,595,647 B2 | 9/2009 | Kroh |
| 7,618,363 B2 | 11/2009 | Yadav |
| 7,621,036 B2 | 11/2009 | Cros |
| 7,621,876 B2 | 11/2009 | Hoctor et al. |
| 7,647,831 B2 | 1/2010 | Corcoran |
| 7,647,836 B2 | 1/2010 | O'Brien |
| 7,662,653 B2 | 2/2010 | O'Brien |
| 7,667,547 B2 | 2/2010 | Ellis |
| 7,677,107 B2 | 3/2010 | Nunez |
| 7,678,135 B2 | 3/2010 | Maahs et al. |
| 7,679,355 B2 | 3/2010 | Allen |
| 7,699,059 B2 | 4/2010 | Fonseca et al. |
| 7,710,103 B2 | 5/2010 | Powers |
| 7,725,160 B2 | 5/2010 | Weber |
| 7,748,277 B2 | 7/2010 | O'Brien |
| 7,778,684 B2 | 8/2010 | Weber et al. |
| 7,786,867 B2 | 8/2010 | Hamel et al. |
| 7,812,416 B2 | 10/2010 | Courcimault |
| 7,829,363 B2 | 11/2010 | You |
| 7,839,153 B2 | 11/2010 | Joy |
| 7,848,813 B2 | 12/2010 | Bergelson et al. |
| 7,854,172 B2 | 12/2010 | O'Brien |
| 7,908,002 B2 | 3/2011 | Hoijer |
| 7,908,018 B2 | 3/2011 | O'Brien |
| 7,909,770 B2 | 3/2011 | Stern et al. |
| 7,932,732 B2 | 4/2011 | Ellis |
| 7,936,174 B2 | 5/2011 | Ellis |
| 7,955,269 B2 | 6/2011 | Stahmann |
| 7,966,886 B2 | 6/2011 | Corcoran et al. |
| 7,988,719 B2 | 8/2011 | Alt et al. |
| 3,021,307 A1 | 9/2011 | White |
| 8,016,766 B2 | 9/2011 | Goedje et al. |
| 8,025,625 B2 | 9/2011 | Allen |
| 8,026,729 B2 | 9/2011 | Kroh |
| 3,060,214 A1 | 11/2011 | Larson et al. |
| 8,078,274 B2 | 12/2011 | Kassab |
| 8,082,032 B2 | 12/2011 | Kassab et al. |
| 8,099,161 B2 | 1/2012 | Kassab |
| 8,107,248 B2 | 1/2012 | Shin et al. |
| 8,111,150 B2 | 2/2012 | Miller |
| 8,114,143 B2 | 2/2012 | Kassab et al. |
| 8,118,749 B2 | 2/2012 | White |
| 8,154,389 B2 | 4/2012 | Rowland |
| 8,159,348 B2 | 4/2012 | Ellis |
| 8,185,194 B2 | 5/2012 | Kassab |
| 8,209,033 B2 | 6/2012 | Zhang et al. |
| 8,221,405 B2 | 7/2012 | Whisenant et al. |
| 8,237,451 B2 | 8/2012 | Joy |
| 8,264,240 B2 | 9/2012 | Park et al. |
| 8,267,954 B2 | 9/2012 | Decant, Jr. et al. |
| 8,278,941 B2 | 10/2012 | Kroh |

(56) References Cited

U.S. PATENT DOCUMENTS

| | | |
|---|---|---|
| 8,298,147 B2 | 10/2012 | Huennekens et al. |
| 8,298,148 B2 | 10/2012 | Furman |
| 8,353,841 B2 | 1/2013 | White |
| 8,355,777 B2 | 1/2013 | White |
| 8,356,399 B2 | 1/2013 | Kaplan |
| 8,360,984 B2 | 1/2013 | Yadav et al. |
| 8,374,689 B2 | 2/2013 | Gopinathan et al. |
| 8,432,265 B2 | 4/2013 | Rowland |
| 8,442,639 B2 | 5/2013 | Walker et al. |
| 8,465,436 B2 | 6/2013 | Griswold |
| 8,465,452 B2 | 6/2013 | Kassab |
| 8,467,854 B2 | 6/2013 | Lewis et al. |
| 8,493,187 B2 | 7/2013 | Rowland |
| 8,500,660 B2 | 8/2013 | Buchwald et al. |
| 8,521,282 B2 | 8/2013 | Czygan et al. |
| 8,527,046 B2 | 9/2013 | Connelly et al. |
| 8,556,929 B2 | 10/2013 | Harper et al. |
| 8,570,186 B2 | 10/2013 | Nagy |
| 8,600,517 B2 | 12/2013 | Forsell |
| 8,613,705 B2 | 12/2013 | Scheurer |
| 8,632,469 B2 | 1/2014 | Kassab |
| 8,644,941 B2 | 2/2014 | Rooney et al. |
| 8,665,086 B2 | 3/2014 | Miller et al. |
| 8,669,770 B2 | 3/2014 | Cros |
| 8,696,584 B2 | 4/2014 | Kassab |
| 8,702,613 B2 | 4/2014 | Kassab |
| 8,706,208 B2 | 4/2014 | Chiao et al. |
| 8,706,209 B2 | 4/2014 | Kassab |
| 8,728,012 B2 | 5/2014 | Braido |
| 8,784,338 B2 | 7/2014 | Wallace |
| 8,798,712 B2 | 8/2014 | Gopinathan et al. |
| 8,814,798 B2 | 8/2014 | Corbucci et al. |
| 8,818,507 B2 | 8/2014 | Liu et al. |
| 8,825,151 B2 | 9/2014 | Gopinathan et al. |
| 8,827,929 B2 | 9/2014 | O'Dea |
| 8,855,783 B2 | 10/2014 | Dagan et al. |
| 8,864,666 B2 | 10/2014 | Kassem |
| 8,870,787 B2 | 10/2014 | Yadav |
| 8,874,203 B2 | 10/2014 | Kassab et al. |
| 8,886,301 B2 | 11/2014 | Kassab |
| 8,894,582 B2 | 11/2014 | Nunez |
| 8,896,324 B2 | 11/2014 | Kroh |
| 8,909,351 B2 | 12/2014 | Dinsmoor et al. |
| 8,918,169 B2 | 12/2014 | Kassab et al. |
| 8,938,292 B2 | 1/2015 | Hettrick et al. |
| 8,951,219 B2 | 2/2015 | Gerber et al. |
| 9,049,995 B2 | 6/2015 | Blomqvist et al. |
| 9,060,798 B2 | 6/2015 | Harper et al. |
| 9,061,099 B2 | 6/2015 | Gerber et al. |
| 9,066,672 B2 | 6/2015 | Kassab et al. |
| 9,198,706 B2 | 12/2015 | Kassab et al. |
| 9,265,428 B2 | 2/2016 | O'Brien et al. |
| 9,289,132 B2 | 3/2016 | Ghaffari et al. |
| 9,289,229 B2 | 3/2016 | Kassab |
| 9,305,456 B2 | 4/2016 | Rowland |
| 9,314,169 B2 | 4/2016 | Kassab |
| 9,326,728 B2 | 5/2016 | Demir et al. |
| 9,332,914 B2 | 5/2016 | Langston |
| 9,332,916 B2 | 5/2016 | Kassab |
| 9,333,365 B2 | 5/2016 | Zhao |
| 9,351,661 B2 | 5/2016 | Kassab |
| 9,393,416 B2 | 7/2016 | Rooney et al. |
| 9,445,743 B2 | 9/2016 | Kassab |
| 9,489,831 B2 | 11/2016 | Nagy et al. |
| 9,526,637 B2 | 12/2016 | Dagan et al. |
| 9,545,263 B2 | 1/2017 | Lenihan et al. |
| 9,603,533 B2 | 3/2017 | Lading et al. |
| 9,662,066 B2 | 5/2017 | Ledet et al. |
| 9,675,257 B2 | 6/2017 | Kassab |
| 9,675,315 B2 | 6/2017 | Song et al. |
| 9,721,463 B2 | 8/2017 | Rowland |
| 9,814,395 B2 | 11/2017 | Stahmann et al. |
| 9,872,948 B2 | 1/2018 | Siess |
| 9,878,080 B2 | 1/2018 | Kaiser et al. |
| 9,901,722 B2 | 2/2018 | Nitzan et al. |
| 9,996,712 B2 | 6/2018 | Sundaram et al. |
| 10,080,528 B2 | 9/2018 | BeBusschere et al. |
| 10,092,247 B2 | 10/2018 | Taylor |
| 10,105,103 B2 | 10/2018 | Goldshtein et al. |
| 10,194,808 B1 | 2/2019 | Thompson |
| 10,195,441 B2 | 2/2019 | Kaiser |
| 10,201,285 B2 | 2/2019 | Sawanoi |
| 10,210,956 B2 | 2/2019 | Lavi |
| 10,213,129 B2 | 2/2019 | Kassab |
| 10,219,704 B2 | 3/2019 | Lavi |
| 10,219,720 B2 | 3/2019 | Kassab |
| 10,219,724 B2 | 3/2019 | Stern |
| 10,226,203 B2 | 3/2019 | Stigall |
| 10,226,218 B2 | 3/2019 | Rowland |
| 10,231,659 B2 | 3/2019 | Vanslyke |
| 10,231,701 B2 | 3/2019 | Ryan |
| 10,236,084 B2 | 3/2019 | Grady |
| 10,238,311 B2 | 3/2019 | Kassab |
| 10,238,322 B2 | 3/2019 | Vanslyke |
| 10,238,323 B2 | 3/2019 | Vanslyke |
| 10,238,324 B2 | 3/2019 | Vanslyke |
| 10,240,994 B1 | 3/2019 | Xu |
| 10,265,024 B2 | 4/2019 | Lee |
| 10,271,797 B2 | 4/2019 | Zhang |
| 10,537,281 B2 | 1/2020 | Thompson et al. |
| 10,542,887 B2 | 1/2020 | Sarkar et al. |
| 10,660,577 B2 | 1/2020 | Thakur et al. |
| 10,548,535 B2 | 2/2020 | Zhang et al. |
| 10,555,704 B2 | 2/2020 | Averina et al. |
| 10,582,866 B2 | 3/2020 | Badie et al. |
| 10,588,528 B2 | 3/2020 | Banet et al. |
| 10,595,734 B2 | 3/2020 | Thakur et al. |
| 10,596,381 B2 | 3/2020 | Averina et al. |
| 10,638,980 B2 | 5/2020 | Gyllensten et al. |
| 10,687,715 B2 | 6/2020 | Jansen et al. |
| 10,702,213 B2 | 7/2020 | Sharma et al. |
| 10,806,352 B2 | 10/2020 | Sweeney et al. |
| 10,905,393 B2 | 2/2021 | Gifford, III et al. |
| 2002/0120205 A1 | 8/2002 | Ferek-Petric |
| 2003/0037591 A1 | 2/2003 | Ashton et al. |
| 2003/0100940 A1 | 5/2003 | Yodfat |
| 2003/0158584 A1 | 8/2003 | Cates et al. |
| 2003/0199938 A1 | 10/2003 | Smits et al. |
| 2004/0054287 A1 | 3/2004 | Stephens |
| 2004/0106871 A1 | 6/2004 | Hunyor et al. |
| 2004/0116992 A1 | 6/2004 | Wardle |
| 2004/0133092 A1 | 7/2004 | Kain |
| 2004/0140939 A1 | 7/2004 | Haller et al. |
| 2004/0167596 A1 | 8/2004 | Richter |
| 2004/0176672 A1 | 9/2004 | Silver et al. |
| 2004/0215235 A1 | 10/2004 | Jackson et al. |
| 2004/0225326 A1 | 11/2004 | Weiner |
| 2005/0137481 A1 | 6/2005 | Sheard et al. |
| 2005/0148903 A1 | 7/2005 | Diamantopoulos |
| 2005/0154321 A1 | 7/2005 | Wolinsky |
| 2006/0047327 A1 | 3/2006 | Colvin et al. |
| 2006/0056161 A1 | 3/2006 | Shin |
| 2006/0079793 A1 | 4/2006 | Mann et al. |
| 2006/0100522 A1 | 5/2006 | Yuan et al. |
| 2006/0106321 A1 | 5/2006 | Lewinsky et al. |
| 2006/0122522 A1 | 6/2006 | Chavan et al. |
| 2006/0149166 A1 | 7/2006 | Zvuloni |
| 2006/0174712 A1 | 8/2006 | O'Brien |
| 2006/0177956 A1 | 8/2006 | O'Brien |
| 2006/0178695 A1 | 8/2006 | Decant |
| 2006/0253160 A1 | 11/2006 | Benditt et al. |
| 2006/0271119 A1 | 11/2006 | Ni et al. |
| 2006/0287602 A1 | 12/2006 | Obrien et al. |
| 2006/0287700 A1 | 12/2006 | White |
| 2007/0088214 A1 | 4/2007 | Shuros et al. |
| 2007/0129637 A1 | 6/2007 | Wolinsky et al. |
| 2007/0158769 A1 | 7/2007 | You |
| 2007/0199385 A1 | 8/2007 | O'Brien |
| 2007/0249950 A1 | 10/2007 | Piaget et al. |
| 2007/0274565 A1 | 11/2007 | Penner |
| 2007/0282210 A1 | 12/2007 | Stern |
| 2007/0292090 A1 | 12/2007 | Alphonse et al. |
| 2008/0015569 A1 | 1/2008 | Saadat |
| 2008/0033527 A1 | 2/2008 | Nunez et al. |

(56) References Cited

U.S. PATENT DOCUMENTS

| | | |
|---|---|---|
| 2008/0077016 A1 | 3/2008 | Sparks |
| 2008/0097227 A1 | 4/2008 | Zdeblick et al. |
| 2008/0177186 A1 | 7/2008 | Slater et al. |
| 2008/0294041 A1 | 11/2008 | Kassab |
| 2009/0007679 A1 | 1/2009 | Nunez |
| 2009/0009332 A1 | 1/2009 | Nunez |
| 2009/0011117 A1 | 1/2009 | Nunez |
| 2009/0024042 A1 | 1/2009 | Nunez |
| 2009/0024177 A1 | 1/2009 | Shuros et al. |
| 2009/0030291 A1 | 1/2009 | O'Brien |
| 2009/0062684 A1 | 3/2009 | Gregersen et al. |
| 2009/0105799 A1 | 4/2009 | Hekmat et al. |
| 2009/0149766 A1 | 6/2009 | Shuros et al. |
| 2009/0177225 A1 | 7/2009 | Nunez et al. |
| 2009/0189741 A1 | 7/2009 | Rowland |
| 2009/0198293 A1 | 8/2009 | Cauller |
| 2009/0270729 A1 | 10/2009 | Corbucci |
| 2009/0299427 A1 | 12/2009 | Liu et al. |
| 2010/0056922 A1 | 3/2010 | Florent |
| 2010/0063375 A1 | 3/2010 | Kassab et al. |
| 2010/0076398 A1 | 3/2010 | Scheurer et al. |
| 2010/0094328 A1 | 4/2010 | O'Dea et al. |
| 2010/0113939 A1 | 5/2010 | Mashimo et al. |
| 2010/0121398 A1 | 5/2010 | Bjorling et al. |
| 2010/0222786 A1 | 9/2010 | Kassab |
| 2010/0262206 A1 | 10/2010 | Zdeblick et al. |
| 2010/0274217 A1 | 10/2010 | Da Silva et al. |
| 2010/0324432 A1 | 12/2010 | Bjorling et al. |
| 2011/0054333 A1 | 3/2011 | Hoffer |
| 2011/0105863 A1 | 5/2011 | Kroh |
| 2011/0144967 A1 | 6/2011 | Adirovich |
| 2011/0160844 A1 | 6/2011 | Haselby |
| 2011/0178383 A1 | 7/2011 | Kassab |
| 2011/0184301 A1 | 7/2011 | Holmstrom et al. |
| 2011/0201990 A1 | 8/2011 | Franano |
| 2011/0224582 A1 | 9/2011 | Spence |
| 2011/0265908 A1 | 11/2011 | Clerc et al. |
| 2011/0306867 A1 | 12/2011 | Gopinathan et al. |
| 2012/0016207 A1 | 1/2012 | Mien |
| 2012/0029598 A1 | 2/2012 | Zhao |
| 2012/0136385 A1 | 5/2012 | Cully |
| 2012/0203090 A1 | 8/2012 | Min |
| 2012/0203113 A1 | 8/2012 | Skerl et al. |
| 2012/0291788 A1 | 11/2012 | Griswold et al. |
| 2012/0296222 A1 | 11/2012 | Griswold et al. |
| 2013/0030295 A1 | 1/2013 | Huennekens et al. |
| 2013/0041244 A1 | 2/2013 | Woias et al. |
| 2013/0041251 A1 | 2/2013 | Bailey et al. |
| 2013/0041269 A1 | 2/2013 | Stahmann et al. |
| 2013/0060139 A1 | 3/2013 | Richter |
| 2013/0073025 A1 | 3/2013 | Kassab |
| 2013/0096409 A1 | 4/2013 | Hiltner et al. |
| 2013/0178750 A1 | 7/2013 | Sheehan et al. |
| 2013/0178751 A1 | 7/2013 | Min |
| 2013/0184545 A1 | 7/2013 | Blomqvist et al. |
| 2013/0218054 A1 | 8/2013 | Sverdlik et al. |
| 2013/0222153 A1 | 8/2013 | Rowland et al. |
| 2013/0245469 A1 | 9/2013 | Yadav |
| 2013/0261655 A1 | 10/2013 | Drasler et al. |
| 2013/0274705 A1 | 10/2013 | Burnes et al. |
| 2013/0281800 A1 | 10/2013 | Saroka et al. |
| 2013/0296721 A1 | 11/2013 | Yadav et al. |
| 2013/0303914 A1 | 11/2013 | Hiltner et al. |
| 2013/0303915 A1 | 11/2013 | Barnard et al. |
| 2013/0310820 A1 | 11/2013 | Fernandez et al. |
| 2013/0317359 A1 | 11/2013 | Wilson et al. |
| 2013/0324866 A1 | 12/2013 | Gladshtein |
| 2013/0331678 A1 | 12/2013 | Lading et al. |
| 2013/0338468 A1 | 12/2013 | Kassab |
| 2014/0028467 A1 | 1/2014 | Nagy |
| 2014/0051965 A1 | 2/2014 | Zdeblick et al. |
| 2014/0066738 A1 | 3/2014 | Kassab |
| 2014/0084943 A1 | 3/2014 | Kroh et al. |
| 2014/0088994 A1 | 3/2014 | Kroh |
| 2014/0094697 A1 | 4/2014 | Petroff et al. |
| 2014/0107768 A1 | 4/2014 | Venkatasubramanian |
| 2014/0155710 A1 | 6/2014 | Rowland |
| 2014/0155768 A1 | 6/2014 | Orion et al. |
| 2014/0155769 A1 | 6/2014 | White |
| 2014/0180118 A1 | 6/2014 | Stigall |
| 2014/0200428 A1 | 7/2014 | Kassab |
| 2014/0236011 A1 | 8/2014 | Fan et al. |
| 2014/0243640 A1 | 8/2014 | O'Dea |
| 2014/0266935 A1 | 9/2014 | Tankiewicz |
| 2014/0275861 A1 | 9/2014 | Kroh et al. |
| 2014/0276011 A1 | 9/2014 | Schmitt et al. |
| 2014/0276067 A1 | 9/2014 | Neasham |
| 2014/0276110 A1 | 9/2014 | Hoseit |
| 2014/0276121 A1 | 9/2014 | Kassab |
| 2014/0276191 A1 | 9/2014 | Kassab |
| 2014/0288085 A1 | 9/2014 | Yadav |
| 2014/0288459 A1 | 9/2014 | Yadav et al. |
| 2014/0306807 A1 | 10/2014 | Rowland |
| 2014/0330143 A1 | 11/2014 | Kroh et al. |
| 2014/0350348 A1 | 11/2014 | Tee et al. |
| 2015/0031966 A1 | 1/2015 | Ward et al. |
| 2015/0045649 A1 | 2/2015 | O'Dea et al. |
| 2015/0051467 A1 | 2/2015 | Corbucci et al. |
| 2015/0065835 A1 | 3/2015 | Kassab |
| 2015/0065897 A1 | 3/2015 | Bornzin et al. |
| 2015/0088100 A1 | 3/2015 | Oborn |
| 2015/0133796 A1 | 5/2015 | Yadav |
| 2015/0141863 A1 | 5/2015 | Kassab et al. |
| 2015/0157268 A1 | 6/2015 | Winshtein et al. |
| 2015/0208929 A1 | 7/2015 | Rowland |
| 2015/0216425 A1 | 8/2015 | Gladshtein et al. |
| 2015/0223702 A1 | 8/2015 | Vanney et al. |
| 2015/0238121 A1 | 8/2015 | Tu et al. |
| 2015/0257732 A1 | 9/2015 | Ryan |
| 2015/0282720 A1 | 10/2015 | Goldshtein et al. |
| 2015/0282875 A1 | 10/2015 | Harper et al. |
| 2015/0290373 A1 | 10/2015 | Rudser et al. |
| 2015/0297110 A1 | 10/2015 | Kassab |
| 2015/0297111 A1 | 10/2015 | Kassab |
| 2015/0297112 A1 | 10/2015 | Kassab et al. |
| 2015/0297113 A1 | 10/2015 | Kassab |
| 2015/0297818 A1 | 10/2015 | Matsubara et al. |
| 2015/0305808 A1 | 10/2015 | Ku et al. |
| 2015/0313479 A1 | 11/2015 | Stigall et al. |
| 2015/0327786 A1 | 11/2015 | Lading et al. |
| 2016/0000403 A1 | 1/2016 | Vilkomerson |
| 2016/0015507 A1 | 1/2016 | Johnson et al. |
| 2016/0022216 A1 | 1/2016 | Goldshtein et al. |
| 2016/0022447 A1 | 1/2016 | Kim et al. |
| 2016/0029956 A1 | 2/2016 | Rowland |
| 2016/0029995 A1 | 2/2016 | Navratil et al. |
| 2016/0038087 A1 | 2/2016 | Hunter |
| 2016/0045184 A1 | 2/2016 | Courtney |
| 2016/0081657 A1 | 3/2016 | Rice |
| 2016/0095535 A1 | 4/2016 | Hettrick et al. |
| 2016/0135787 A1 | 5/2016 | Anderson et al. |
| 2016/0135941 A1 | 5/2016 | Binmoeller et al. |
| 2016/0166232 A1 | 6/2016 | Merritt |
| 2016/0198981 A1 | 7/2016 | Demir et al. |
| 2016/0210846 A1 | 7/2016 | Rowland et al. |
| 2016/0324443 A1 | 11/2016 | Rowland et al. |
| 2016/0345930 A1 | 12/2016 | Mizukami |
| 2017/0055048 A1 | 2/2017 | Nagy et al. |
| 2017/0055909 A1 | 3/2017 | Schibli et al. |
| 2017/0065186 A1 | 3/2017 | Joseph et al. |
| 2017/0071501 A1 | 3/2017 | Kassab |
| 2017/0127975 A1 | 5/2017 | Bozkurt |
| 2017/0181677 A1 | 6/2017 | Varsavsky et al. |
| 2017/0065824 A1 | 8/2017 | Dagan et al. |
| 2017/0216508 A1 | 8/2017 | Zilbershlag et al. |
| 2017/0238817 A1 | 8/2017 | Lading |
| 2017/0290686 A1 | 10/2017 | Sirhan et al. |
| 2017/0319096 A1 | 11/2017 | Kaiser |
| 2017/0360312 A1 | 12/2017 | Joseph |
| 2018/0014829 A1 | 1/2018 | Tal et al. |
| 2018/0064931 A1 | 3/2018 | Clements |
| 2018/0172785 A1 | 6/2018 | Leussler et al. |
| 2018/0177486 A1 | 6/2018 | Gifford et al. |
| 2018/0220992 A1 | 8/2018 | Gifford et al. |

(56) References Cited

U.S. PATENT DOCUMENTS

| | | |
|---|---|---|
| 2018/0228951 A1 | 8/2018 | Schwammenthal et al. |
| 2018/0247095 A1 | 8/2018 | Sundaram et al. |
| 2018/0268941 A1 | 9/2018 | Lavi et al. |
| 2018/0269931 A1 | 9/2018 | Hershko et al. |
| 2018/0289488 A1 | 10/2018 | Orth et al. |
| 2018/0289536 A1 | 10/2018 | Burnett |
| 2018/0293409 A1 | 10/2018 | Sundaram et al. |
| 2018/0326151 A1 | 11/2018 | Halpert et al. |
| 2018/0344917 A1 | 12/2018 | Inhaber et al. |
| 2019/0015013 A1 | 1/2019 | Zhu et al. |
| 2019/0029639 A1 | 1/2019 | Gifford et al. |
| 2019/0046047 A1 | 2/2019 | Haase |
| 2019/0053720 A1 | 2/2019 | Sawado |
| 2019/0053767 A1 | 2/2019 | Kamada |
| 2019/0059777 A1 | 2/2019 | Aga et al. |
| 2019/0069784 A1 | 3/2019 | Mukkamala |
| 2019/0069842 A1 | 3/2019 | Rothberg |
| 2019/0069851 A1 | 3/2019 | Sharma |
| 2019/0070348 A1 | 3/2019 | Frost |
| 2019/0076033 A1 | 3/2019 | Sweeney et al. |
| 2019/0082978 A1 | 3/2019 | Van der Horst |
| 2019/0083030 A1 | 3/2019 | Thakur |
| 2019/0090760 A1 | 3/2019 | Kinast |
| 2019/0090763 A1 | 3/2019 | Woerlee |
| 2019/0090856 A1 | 3/2019 | Van der Horst |
| 2019/0099087 A1 | 4/2019 | Cros |
| 2019/0099088 A1 | 4/2019 | Whinnett |
| 2019/0110696 A1 | 4/2019 | Benkowski |
| 2019/0126014 A1 | 5/2019 | Kapur et al. |
| 2019/0150884 A1 | 5/2019 | Maharbiz et al. |
| 2019/0167188 A1 | 6/2019 | Gifford et al. |
| 2019/0358393 A1 | 11/2019 | Marbet |
| 2020/0000364 A1 | 1/2020 | Doodeman et al. |
| 2020/0013510 A1 | 1/2020 | Despenic et al. |
| 2020/0022588 A1 | 1/2020 | Wariar et al. |
| 2020/0022589 A1 | 1/2020 | Banet et al. |
| 2020/0029829 A1 | 1/2020 | Banet et al. |
| 2020/0029857 A1 | 1/2020 | Rowland et al. |
| 2020/0030612 A1 | 1/2020 | Song et al. |
| 2020/0037888 A1 | 2/2020 | Thakur et al. |
| 2020/0037892 A1 | 2/2020 | Banet et al. |
| 2020/0046299 A1 | 2/2020 | An et al. |
| 2020/0069857 A1 | 3/2020 | Schwammenthal et al. |
| 2020/0121187 A1 | 4/2020 | Sarkar et al. |
| 2020/0129087 A1 | 4/2020 | Sweeney et al. |
| 2020/0146577 A1 | 5/2020 | Badie et al. |
| 2020/0170515 A1 | 6/2020 | Wen et al. |
| 2020/0170711 A1 | 6/2020 | Hendriks et al. |
| 2020/0187864 A1 | 6/2020 | Sharma |
| 2020/0187865 A1 | 6/2020 | Sharma et al. |
| 2020/0196876 A1 | 6/2020 | Minor et al. |
| 2020/0196899 A1 | 6/2020 | Higgins et al. |
| 2020/0196943 A1 | 6/2020 | Minor et al. |
| 2020/0196944 A1 | 6/2020 | Minor et al. |
| 2020/0196948 A1 | 6/2020 | Cho et al. |
| 2020/0197178 A1 | 6/2020 | Vecchio |
| 2020/0254161 A1 | 8/2020 | Schwammenthal et al. |
| 2020/0289257 A1 | 9/2020 | Marquez |

FOREIGN PATENT DOCUMENTS

| | | |
|---|---|---|
| EP | 0538885 A1 | 4/1993 |
| EP | 0897285 A1 | 2/1999 |
| EP | 1162914 A1 | 12/2001 |
| EP | 1311210 A2 | 5/2003 |
| EP | 0904009 B1 | 9/2003 |
| EP | 1545303 A2 | 6/2005 |
| EP | 1677852 A2 | 7/2006 |
| EP | 1847217 A2 | 10/2007 |
| EP | 1851524 A2 | 11/2007 |
| EP | 1851791 A2 | 11/2007 |
| EP | 1868496 A2 | 12/2007 |
| EP | 1871224 A2 | 1/2008 |
| EP | 1893080 A2 | 3/2008 |
| EP | 1893081 A2 | 3/2008 |
| EP | 1893085 A2 | 3/2008 |
| EP | 2091426 A2 | 6/2008 |
| EP | 1948007 | 7/2008 |
| EP | 1993438 A1 | 11/2008 |
| EP | 2012658 A2 | 1/2009 |
| EP | 2046242 A2 | 4/2009 |
| EP | 2117423 A2 | 11/2009 |
| EP | 2197344 A1 | 6/2010 |
| EP | 2265164 A1 | 12/2010 |
| EP | 2021757 B1 | 4/2011 |
| EP | 2391263 A2 | 12/2011 |
| EP | 1921983 B1 | 1/2012 |
| EP | 2060014 B1 | 1/2012 |
| EP | 1902529 B1 | 6/2012 |
| EP | 1876945 B1 | 12/2012 |
| EP | 2330968 B1 | 4/2013 |
| EP | 2601633 A2 | 6/2013 |
| EP | 2449960 B1 | 10/2013 |
| EP | 2725969 A1 | 5/2014 |
| EP | 1993436 B1 | 6/2014 |
| EP | 3027109 A1 | 2/2015 |
| EP | 2076170 B1 | 4/2015 |
| EP | 2895059 A1 | 7/2015 |
| EP | 2898470 A1 | 7/2015 |
| EP | 2922465 A1 | 9/2015 |
| EP | 2317912 B1 | 11/2015 |
| EP | 1817593 B1 | 12/2015 |
| EP | 2967432 A2 | 1/2016 |
| EP | 2268218 B1 | 2/2016 |
| EP | 2456502 B1 | 4/2016 |
| EP | 2702578 B1 | 8/2016 |
| EP | 3057075 A1 | 8/2016 |
| EP | 2417590 B1 | 5/2017 |
| EP | 2986252 B1 | 7/2018 |
| EP | 3359021 A1 | 8/2018 |
| EP | 3435847 A1 | 2/2019 |
| EP | 3435862 A1 | 2/2019 |
| EP | 3437000 A1 | 2/2019 |
| EP | 3448330 A1 | 3/2019 |
| EP | 3448487 A2 | 3/2019 |
| EP | 3457911 A1 | 3/2019 |
| EP | 3457924 A1 | 3/2019 |
| EP | 3457928 A1 | 3/2019 |
| EP | 3463082 A1 | 4/2019 |
| EP | 3468462 A1 | 4/2019 |
| EP | 3591663 A1 | 1/2020 |
| EP | 3609392 A1 | 2/2020 |
| EP | 3256043 B1 | 3/2020 |
| EP | 3629921 A1 | 4/2020 |
| EP | 3629937 A1 | 4/2020 |
| EP | 3630275 A1 | 4/2020 |
| EP | 3634206 A1 | 4/2020 |
| EP | 3654835 A1 | 5/2020 |
| EP | 3496808 B1 | 6/2020 |
| EP | 2654560 B1 | 7/2020 |
| EP | 3326524 B1 | 7/2020 |
| EP | 3367884 B1 | 7/2020 |
| EP | 3678539 A1 | 7/2020 |
| EP | 3681389 A1 | 7/2020 |
| EP | 3684260 A1 | 7/2020 |
| EP | 3684464 A1 | 7/2020 |
| GB | 2473529 A | 3/2011 |
| JP | 2011234884 A | 11/2011 |
| WO | 1997042871 A1 | 11/1997 |
| WO | 1998029030 A1 | 12/1997 |
| WO | 1998035611 A1 | 8/1998 |
| WO | 2000055579 A2 | 9/2000 |
| WO | 2000056210 A1 | 9/2000 |
| WO | 2001012092 A1 | 2/2001 |
| WO | 2001013792 A1 | 3/2001 |
| WO | 2002015823 A2 | 2/2002 |
| WO | 2002076289 A2 | 10/2002 |
| WO | 2003061467 A1 | 7/2003 |
| WO | 2003061504 A1 | 7/2003 |
| WO | 2003092495 A1 | 11/2003 |
| WO | 2004014456 A2 | 2/2004 |
| WO | 2004073796 A1 | 9/2004 |
| WO | 2006049796 A2 | 5/2006 |
| WO | 2006086113 A2 | 8/2006 |

(56) References Cited

FOREIGN PATENT DOCUMENTS

| | | | |
|---|---|---|---|
| WO | 2006086114 A2 | 8/2006 | |
| WO | 2005027998 A2 | 9/2006 | |
| WO | 2006094273 A2 | 9/2006 | |
| WO | 2006096582 A1 | 9/2006 | |
| WO | 2006102905 A1 | 10/2006 | |
| WO | 2006110798 A2 | 10/2006 | |
| WO | 2007002185 A2 | 1/2007 | |
| WO | 2007002224 A2 | 1/2007 | |
| WO | 2007002225 A2 | 1/2007 | |
| WO | 2007008493 A1 | 1/2007 | |
| WO | 2007028035 A2 | 3/2007 | |
| WO | 2007035332 A1 | 3/2007 | |
| WO | 2007047571 A2 | 4/2007 | |
| WO | 2007047794 A2 | 4/2007 | |
| WO | 2007061841 A2 | 5/2007 | |
| WO | 2007106490 A2 | 9/2007 | |
| WO | 2007106533 A1 | 9/2007 | |
| WO | 2007130628 A2 | 11/2007 | |
| WO | 2008031011 A1 | 3/2008 | |
| WO | 2008031095 A1 | 3/2008 | |
| WO | 2008051907 A1 | 5/2008 | |
| WO | 2008066569 A2 | 6/2008 | |
| WO | 2009006602 A1 | 1/2009 | |
| WO | 2009006608 A1 | 1/2009 | |
| WO | 2009006610 A1 | 1/2009 | |
| WO | 2009006615 A1 | 1/2009 | |
| WO | 2009025648 A1 | 2/2009 | |
| WO | 2009039174 A1 | 3/2009 | |
| WO | 2009111255 A1 | 9/2009 | |
| WO | 2009131879 A1 | 10/2009 | |
| WO | 2011060359 A2 | 11/2009 | |
| WO | 2009146089 A2 | 12/2009 | |
| WO | 2009146090 A1 | 12/2009 | |
| WO | 2009149462 A2 | 12/2009 | |
| WO | 2010011612 A1 | 1/2010 | |
| WO | 2010088279 A2 | 8/2010 | |
| WO | 2010117597 A1 | 10/2010 | |
| WO | 20100117356 A1 | 10/2010 | |
| WO | 2011011104 A1 | 1/2011 | |
| WO | 2012015954 A1 | 2/2012 | |
| WO | 2012015955 A1 | 2/2012 | |
| WO | 2012019191 A2 | 2/2012 | |
| WO | 2012090206 A2 | 7/2012 | |
| WO | 2012140147 A3 | 10/2012 | |
| WO | 2012145187 A1 | 10/2012 | |
| WO | 2012149008 A2 | 11/2012 | |
| WO | 2013003754 A1 | 1/2013 | |
| WO | 2013142387 A1 | 9/2013 | |
| WO | 2014006471 A2 | 1/2014 | |
| WO | WO-2014012076 A1 * | 1/2014 | ........... A61B 5/0537 |
| WO | 2004014456 A2 | 2/2014 | |
| WO | 2014047528 A1 | 3/2014 | |
| WO | 2014054045 A1 | 4/2014 | |
| WO | 2014070316 A1 | 5/2014 | |
| WO | 2014076620 A2 | 5/2014 | |
| WO | 2014081958 A1 | 5/2014 | |
| WO | 2014145531 A1 | 9/2014 | |
| WO | 2014145712 A1 | 9/2014 | |
| WO | 2014162181 A2 | 10/2014 | |
| WO | 2014170771 A1 | 10/2014 | |
| WO | 2014179739 A1 | 11/2014 | |
| WO | 2014188430 A2 | 11/2014 | |
| WO | 2014197101 A1 | 12/2014 | |
| WO | 2015074018 A1 | 5/2015 | |
| WO | 2015109028 A1 | 7/2015 | |
| WO | 2015015//12 A2 | 10/2015 | |
| WO | 2016011309 A2 | 1/2016 | |
| WO | 2016025430 A1 | 2/2016 | |
| WO | 2016131020 A1 | 8/2016 | |
| WO | WO-2016156446 A1 * | 10/2016 | ............... A61B 8/06 |
| WO | 2016178196 A2 | 11/2016 | |
| WO | 2016178197 A1 | 11/2016 | |
| WO | 2017024051 A1 | 2/2017 | |
| WO | WO-2017024051 A1 * | 2/2017 | ........... A61B 5/1076 |
| WO | 2017143198 A1 | 8/2017 | |
| WO | 2017198867 A1 | 11/2017 | |
| WO | 2017222964 A1 | 12/2017 | |
| WO | 2018013725 A1 | 1/2018 | |
| WO | 2018031714 A1 | 2/2018 | |
| WO | 2018081314 A1 | 5/2018 | |
| WO | 2018102435 A1 | 6/2018 | |
| WO | 2018150314 A1 | 8/2018 | |
| WO | 2018156930 A1 | 8/2018 | |
| WO | 2018187582 A1 | 10/2018 | |
| WO | 2018220143 A1 | 12/2018 | |
| WO | 2018220146 A1 | 12/2018 | |
| WO | 2019050831 A1 | 3/2019 | |
| WO | 2019051007 A1 | 3/2019 | |
| WO | 2019051108 A1 | 3/2019 | |
| WO | 2019051007 A8 | 4/2019 | |
| WO | 2019063521 A1 | 4/2019 | |
| WO | 2019079364 A1 | 4/2019 | |
| WO | 2020023839 A1 | 1/2020 | |
| WO | 2020121221 A1 | 6/2020 | |
| WO | 2020131247 A1 | 6/2020 | |
| WO | 2020132460 A1 | 6/2020 | |
| WO | 2020132668 A2 | 6/2020 | |
| WO | 2020132669 A1 | 6/2020 | |
| WO | 2020132670 A1 | 6/2020 | |
| WO | 2020132671 A1 | 6/2020 | |
| WO | 2020132678 A1 | 6/2020 | |
| WO | 2020144075 A1 | 7/2020 | |
| WO | 2020153765 A2 | 7/2020 | |

OTHER PUBLICATIONS

International Search Report and Written Opinion dated Mar. 27, 2018, in connection with PCT/US2017/063749.
International Search Report and Written Opinion dated Aug. 29, 2018, in connection with PCT/EP2018/064386.
International Search Report and Written Opinion dated Aug. 21, 2018, in connection with PCT/EP2018/064383.
Extended European Search Report dated Sep. 16, 2020, in connection with EP Application No. 20178613.4, filed Nov. 29, 2017.
International Search Report and Written Opinion dated Oct. 19, 2017, in connection with PCT/US2017/046204.
Brennan, J.M., "Handcarried Ultrasound Measurement of the Inferior Vena Cava for Assessment of Intravascular Volume Status in the Outpatient Hemodialysis Clinic"; Clinical Journal of the American Society of Nephrology; pp. 749-753; Jan. 23, 2006.
International Search Report and Written Opinion dated Oct. 20, 2016, in connection with PCT/US2016/045385 filed Aug. 3, 2016.
ISR Report and Written Opinion dated Dec. 30, 2020, in connection with PCT/EP2020/067713 filed on Jun. 24, 2020.
International Search Report and Written Opinion dated Nov. 4, 2019, in connection with PCT/US2019/034657, filed May 30, 2019.
Voroneanu et al., "The relationship between chronic volume overload 3 and elevated blood pressure in hemodialysis patients: 4 use of bioimpedance provides a different perspective 5 from echocardiography and biomarker methodologies," Int Urol Nephrol, Sep. 2010; 42(3):789-97.
Cannesson et al., "Respiratory Variations in Pulse Oximetry Plethysmographic Waveform Amplitude to Predict Fluid Responsiveness in the Operating Room," Anesthesiology 2007; 106:1105-11.
Abraham et al., "The Role of Implantable Hemodynamic Monitors to Manage Heart Failure," Heart Failure Clin 11 (2015) 183-189.
Tallaj et al., "Implantable Hemodynamic Monitors," Cardiol Clin 29 (2011) 289-299.
Tang et al., "Measuring impedance in congestive heart failure: Current options and clinical applications," American Heart Journal 157 (3) 402-411.
Merchant et al., "Implantable Sensors for Heart Failure," Circulation: Arrhythmia and Electrophysiology. 2010; 3: 657-667.
Unadkat, Jignesh V., et al. "The Development of a Wireless Implantable Blood Flow Monitor," Ideas and Innovations, American Society of Plastic Surgeons, 136:199 (2015).
Steinhouse, David et al., "Implant Experience with an Implantable Hemodynamic Monitor for the Management of Symptomatic Heart Failure," PACE (Aug. 2005) vol. 28, pp. 747-753.

(56) References Cited

OTHER PUBLICATIONS

Braunschweig, Frieder et al. "Dynamic changes in right ventricular pressures during haemodialysis recorded with an implantable haemodynamic monitor," Nephrol Dial Transplant (2006) 21:176-183.
Karamanoglu, Mustafa et al., "Estimation of cardiac output in patients with congestive heart failure by analysis of right ventricular pressure waveforms," BioMedical Engineering Online 2011, 10:36.
Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.
Sharma, Arjun D. et al., "Right Ventricular Pressure During Ventricular Arrhythmias in Humans: Potential Implications for Implantable Antitachycardia Devices," JACC vol. 15, No. 3, Mar. 1, 1990, pp. 648-655.
Kjellstrom, Barbo et al., "Changes in Right Ventricular Pressures Between Hemodialysis Sessions Recorded by an Implantable Hemodynamic Monitor," The American Journal of Cardiology, 2009, 103:119-123.
Zile, Michael R. et al., "Transition From Chronic Compensated to Acute Decompensated Heart Failure," Circulation, American Heart Association (2008) 118:1433-1441.
Plicchi, G. et al., "Pea I and Pea II Based Implantable Haemodynamic Monitor: Pre Clinical Studies in Sheep," Europace (2002) 4, 49-54.
Vanderheyden, Marc et al., "Continuous Monitoring of Intrathoracic Impedance and Right Ventricular Pressures in Patients With Heart Failure," Circulation Heart Failure (2010) 3:370-377.
Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.
Muller, Laurent et al., "Respiratory variations of inferior vena cava diameter to predict fluid responsiveness in spontaneously breathing patients with acute circulatory failure: need for a cautious use," Critical Care 2012, 16:R188.
Blehar, David J. et al., "Identification of congestive heart failure via respiratory variation of inferior vena cava diameter." American Journal of Emergency Medicine (2009) 27, 71-75.
Miller, Joseph B., et al., "Inferior vena cava assessment in the bedside diagnosis of acute heart failure," American Journal of Emergency Medicine (2012) 30, 778-783.
Corl, Keith et al., "Bedside sonographic measurement of the inferior vena cava caval index is a poor predictor of fluid responsiveness in emergency department patients," Emergency Medicine Australasia (2012) 24, 534-539.
Feissel, et al. "The respiratory variation in inferior vena cava diameter as a guide to fluid therapy," Intensive Care Med (2004) 30: 1834-1837.
Nakao, Shoichiro et al., "Effects of Positional Changes on Inferior Vena Caval Size and Dynamics and Correlations with Right-Sided Cardiac Pressure," American Journal of Cardiology (1987; 59:125-132).
Saha, Narayan M., et al., "Outpatient Use of Focused Cardiac Ultrasound to Assess the Inferior Vena Cava in Patients With Heart Failure," American Journal of Cardiology (2015).
Shizaki, et al. "Measurement of inferior vena cava diameter for evaluation of venous return in subjects on day 10 of a bed-rest experiment," J Appl Physical 96: 2179-2186, 2004.
Carbone et al. "Inferior Vena Cava Parameters Predict Re-admission in Ischaemic Heart Failure", European Journal of Clinical Investigations, 2014, 44(4): 341-349.
Bertram, C.D. et al., "Cross-sectional area measurement in collapsed tubes using the transformer principle", Med. & Biol, Eng. & Comput, 1989, 27, 357-364.

Moreno, Augusto et al., "Mechanics of Distension of Dog Veins and Other Very Thin-Walled Tubular Structures", Circulation Research, vol. XXVII, Dec. 1970, pp. 1069-1080.
Tafur, Emilio et al., "Simultaneous Pressure, Flow and Diameter of the Vena Cava with Fright and Exercise", Circulation Research, vol. XIX, Jul. 1966., pp. 42-50.
Guntheroth, Warren G., et al., "Effect of Respiration on Venous Return and Stroke Volume in Cardiac Tamponade", Circulation Research, vol. XX, Apr. 1967, pp. 381-390.
Bartels, Lambertus et al., "Improved Lumen Visualization in Metallic Vascular Implants by Reducing RF Artifacts", Magnetic Resonance in Medicine 47:171-180 (2002).
Guntheroth, Warren G., "in Vivo Measurement of Dimensions of Veins with Implications Regarding Control of Venous Return", IEEE Transactions on Bio-Medical Engineering, Oct. 1969; pp. 247-253.
Kivelitz, Dietmar et al., "A Vascular Stent as an Active Component for Locally Enhanced Magnetic Resonance Imaging", Investigative Radiology, vol. 38, No. 3, 147-152 (2003).
Reddy, Reddy R.V., et al., "A Catheter-Tip Probe for Dynamic Cross-Section Area Measurement", pp. 149-158. (1973).
Stegall, H. Fred, "Survey of Dimension Transducers", Chronically Implanted Cardiovascular Instrumentation, pp. 107-115 (1973).
D. H. Bergel, "The Measurement of Lengths and Dimensions", Cardiovascular Fluid Dynamics, vol. 1. pp. 91-114 (1972).
Baan, Jan et al., "Dynamic Local Distensibility of Living Arteries and its relation to Wave Transmission", Biophysical Journal, vol. 14, (1974); pp. 343-362.
International Search Report and Written Opinion in connection with PCT/US2016/017902, dated Jul. 27, 2016.
Reems, Miryam et al., Central Venous Pressure: Principles, Measurement, and Interpretation, Vetlearn.com, Jan. 2012, Compendium: Continuing Education for Veterinarians, pp. E1-E10.
Yamauchi, Hideko et al., "Correlation Between Blood Volume and Pulmonary Artery Catheter Measurements", Department of Surgery and Surgical Critical Care, University of Hawaii, 2005.
Abraham, William T. et al., "Wireless pulmonary artery haemodynamic monitoring in chronic heart failure: a randomised controlled trial"; www.thelancet.com, vol. 377, Feb. 19, 2011, pp. 658-666.
Guiotto, Giovanna et al., "Inferior vena cava collapsibility to guide fluid removal in slow continuous ultrafiltration: a pilot study", Intensive Care Med (2010) 36:696-696.
Martens, Pieter et al., "Current Approach to Decongestive Therapy in Acute Heart Failure", Curr Heart Fail Rep (2015) 12:367-378.
Dupont, Matthias et a., "Impact of Systemic Venous Congestion in Heart Failure", Curr Heart Fail Rep (2011) 8:233-241.
Marik, Paul E. et al., "Hemodynamic parameters to guide fluid therapy", Annals of Intensive Care 2011, 1:1; http://www.annalsofintensivecare.com/content/1/1/1.
Silverberg, Donald et al., "The association between congestive heart failure and chronic renal disease", Curr Opin Nephrol Hypertens 13: 163-170, 2004.
Horizon Scanning Research & Intelligence Centre; Furosemide sc2Wear micro-pump patch for oedema in heart failure; National Institute for Health Research; NIHR HSRIC ID: 11808; Mar. 2016; pp. 1-10; www.hsric.nihr.ac.uk.
Extended European Search Report dated Jul. 3, 2020, in connection with EP20163433.4.
International Search Report and Written Opinion dated Feb. 27, 2020, in connection with PCT/IB2019/060669 filed Dec. 11, 2019.
International Search Report and Written Opinion dated Feb. 18, 2021, in connection with PCT/IB2020/060669, filed Nov. 12, 2020.
International Search Report and Written Opinion dated Jan. 19, 2021, in connection with PCT/EP2020/079939, filed Oct. 23, 2020.

\* cited by examiner

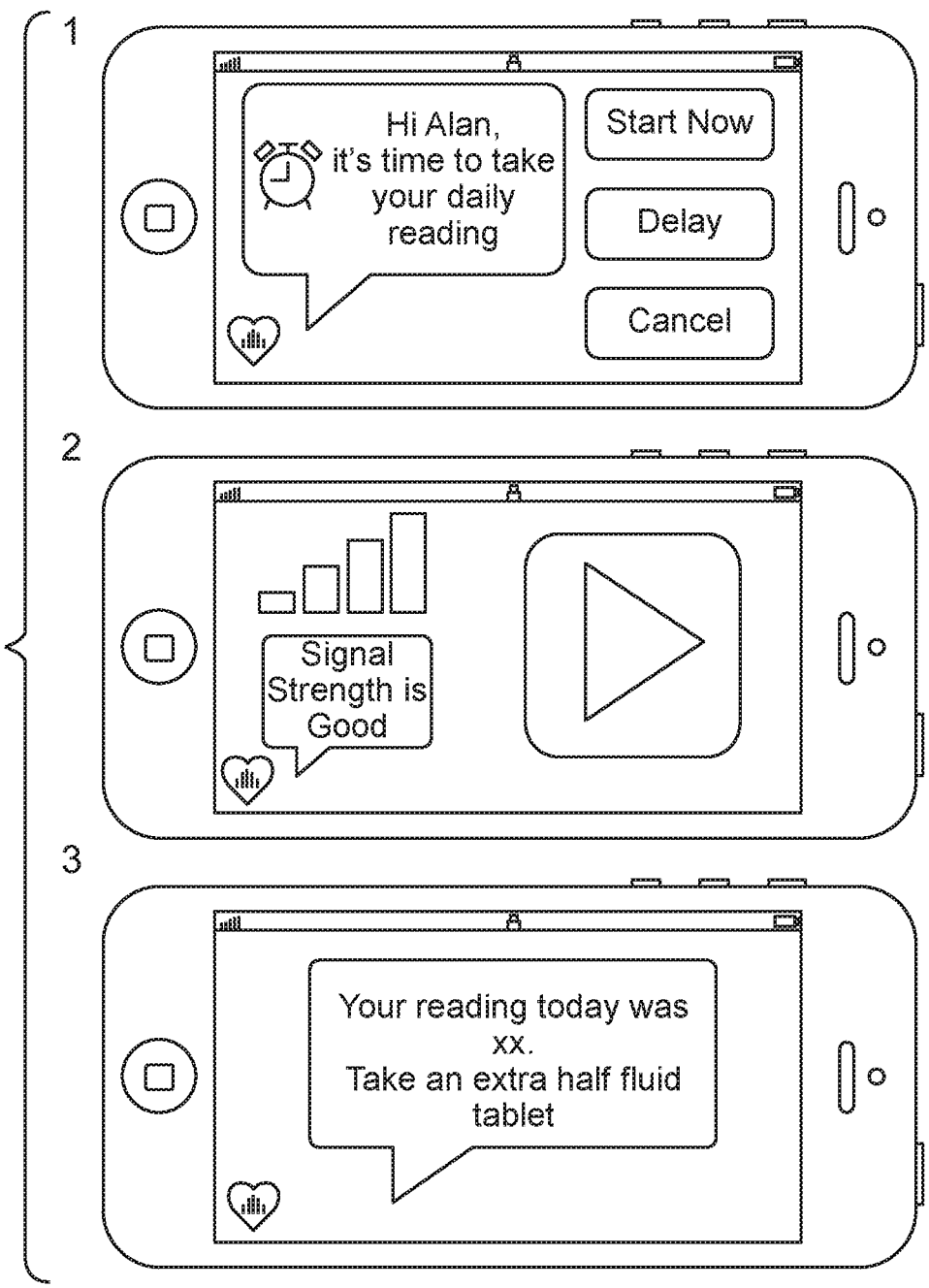

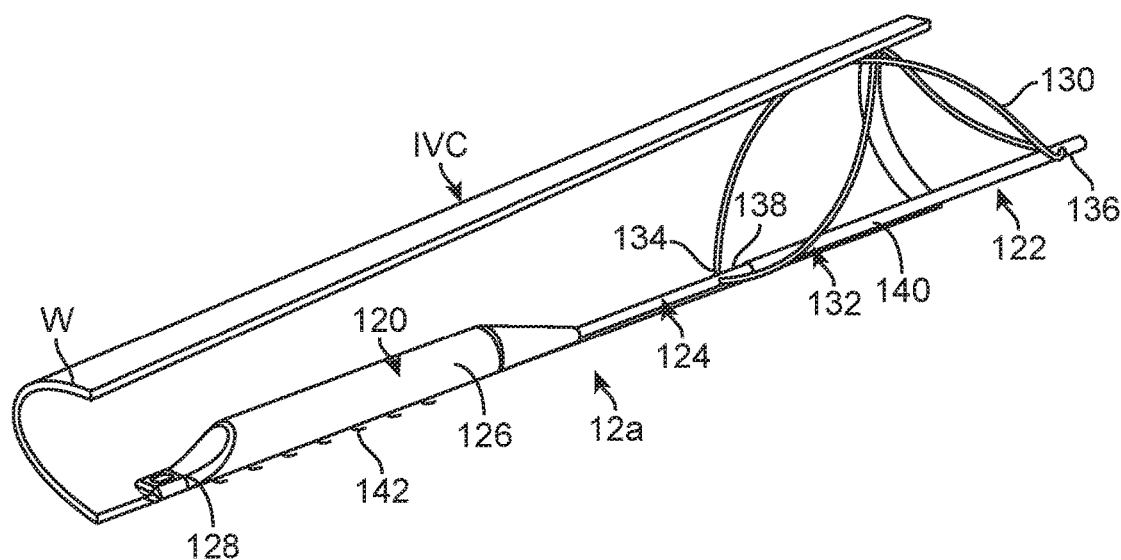
FIG. 12A
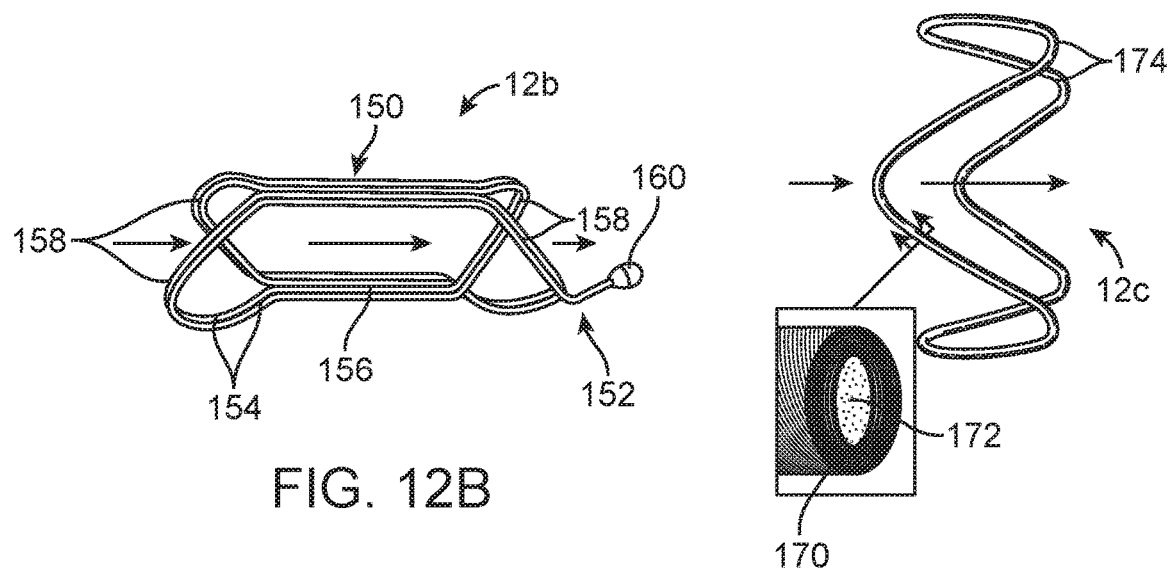
FIG. 12B
FIG. 12C

SYSTEMS AND METHODS FOR PATIENT FLUID MANAGEMENT

RELATED APPLICATION DATA

This application is a continuation of PCT/US017/046204, filed Aug. 10, 2017, entitled Systems and Methods for Patient Fluid Management, which PCT application claims the benefit of priority of U.S. Provisional Patent Application Ser. No. 62/373,436, filed Aug. 11, 2016, and titled "Methods and Systems For Patient Fluid Management", this application also claims the benefit of priority of U.S. Provisional Patent Application Ser. No. 62/427,631, filed Nov. 29, 2016, and titled "Wireless Vascular Monitoring Implants, Systems, Methods, and Software", and also claims the benefit of priority of U.S. Provisional Patent Application No. 62/534,329, filed Jul. 19, 2017, and titled "Wireless Vascular Monitoring Implants, Systems and Methods". Each of these applications is incorporated by reference herein in their entirety.

FIELD OF THE DISCLOSURE

Embodiments disclosed herein relate to systems and methods for patient fluid management, for example in connection with heart failure or renal failure conditions, as well as other disease states requiring careful management of patient fluid balance.

BACKGROUND

A significant challenge in the treatment of acute heart failure patients is the management of the patient fluid volume. Similar challenges are also presented in the treatment of renal failure patients, and, in fact, studies have shown a direct correlation, and potentially causal relationship, between heart and renal failure conditions with respect to patient fluid management [e.g., Silverberg, et al., *The association between congestive heart failure and chronic renal disease*, Curr. Opin. Nephrol. Hypertens. (2004) 13:163-170]. Acute heart or renal failure can lead to peripheral and pulmonary edema if not properly treated, but too aggressive of a treatment can lead to a hypovolemic state in which the patient lacks sufficient fluid volume. Treatments may include dialysis, ultrafiltration, diuretics and other drug administration. For longer term patients, fluid and dietary intake also may be monitored and modulated. Traditionally, diagnostic techniques used in monitoring fluid status were based on various externally observable symptoms (e.g., jugular vein distention, edema, patient weight change). Also, central venous catheterization (CVC) to monitor central venous pressure (CVP) has been used as a fluid status indicator. However, there are a number of serious risks associated with CVC, such as infection and thrombosis, and reliance on externally observable or measurable symptoms presents an obvious drawback in that the observable response to a therapy is often significantly delayed relative to acute changes in physiological status.

Monitoring fluid status can also be used as a predictor for onset of acute decompensated heart failure (ADHF), which is a significant factor driving rehospitalization of heart failure patients. There is potential to significantly reduce hospitalizations if there is a sufficiently early signal of increasing patient fluid volume. However, drawbacks of traditional diagnostic tools as mentioned above make such tools relatively ineffective as early predictors of ADHF.

In an attempt to overcome risks and drawbacks associated with more traditional diagnostic techniques, different types of diagnostic devices or techniques have been developed to measure central venous pressure (CVP) [e.g., Shuros, et al., Coronary Vein Hemodynamic Sensor, US 20090/01497666, Jun. 11, 2009] or pulmonary artery pressure (PAP) [e.g., Abraham, et al., *Wireless pulmonary artery haemodynamic monitoring in chronic heart failure: a randomized controlled trial*, Lancet (2011) 377:658-66]. Also, research using external ultrasound observation of the Inferior Vena Cava (IVC) has led to a general understanding of a correlation between the IVC volume and patient health in terms of proper fluid balance [e.g., Feissel et al., *The respiratory variation in inferior vena cava diameter as a guide to fluid therapy*, Intensive Care Med (2004) 30:1834-1837]. Based on this understanding, external ultrasound systems are now sometimes used in emergency treatment situations to provide the attending physicians with information on patient fluid state. In addition, more recent techniques have been proposed in which devices indirectly measure vessel pressure or volume based on changes in impedance in response to an applied current within the vessel.

While devices and techniques now available may offer advantages over more traditional techniques based on observation of externally visible symptoms, each has its own disadvantages that limit effectiveness as a diagnostic tool to support more aggressive therapies. Many newer monitoring devices or techniques either do not provide sufficiently accurate data to allow early warning of changes in patient stability or do not provide guidance with respect to a particular type of intervention [see, e.g., Marik, et al., *Does Central Venous Pressure Predict Fluid Responsiveness?\*: A Systematic Review of the Literature and the Tale of Seven Mares*, Chest (2008) 134(1):172-178]. Examples include that impedance-based devices have not shown sufficient sensitivity and PAP measurements do not provide a warning of hypovolemia. External measurement of IVC dimensions with external ultrasound systems is heavily reliant on proper and consistent positioning of the patient and the imaging device, both initially and over the period of monitoring, and may not always provide accurate prediction of fluid state [e.g., Blehar, et al, *Inferior vena cava displacement during respirophasic ultrasound imaging*, Critical Ultrasound Journal (2012) 4:18]. It is also impractical for use as a longer term diagnostic tool for regular (e.g. daily) monitoring of patients who are not hospitalized.

SUMMARY OF THE DISCLOSURE

Embodiments disclosed herein include a system for managing patient body fluid volume, comprising a wireless sensing device, a sensing control module and a patient management system. The wireless sensing device is configured to be positioned within a patient's IVC to measure a physical dimension of the IVC and generate a measurement signal indicative of the measured IVC physical dimension. The sensing device control module is configured to wirelessly communicate with the sensing device to at least receive the measurement signal from the sensing device. The patient management system may include a processor and memory, and is configured to receive or generate measurement data representative of the measured IVC physical dimension based on the measurement signal, to receive patient specific information, and to execute instructions contained in the memory responsive to received patient specific information and the measurement data. The instructions contained in memory may include instructions to prompt for initiation of a sensor measurement of the IVC physical dimension and generate an alert signal when the measured IVC physical dimension is outside predetermined clinical limits for the patient. The instructions may further include instructions to wirelessly communicate with the implanted sensing device to monitor changes in the measured IVC dimension throughout an euvolemic region defined for said patient. In some embodiments, the physical dimension of the patient's IVC is at least one of IVC diameter or IVC area.

In another, alternative embodiment, a system for managing patient body fluid volume includes a processor and memory configured to communicate with the implanted wireless sensing device and the sensing device control module. The processor may be configured to receive measurement data representing the IVC physical dimension measurement by the sensing device and execute instructions contained in the memory responsive that measurement data. The processor also may be configured to receive patient specific information. The instructions stored in memory may comprise defining euvolemic, hypovolemic and hypervolemic regions for the patient wherein the euvolemic range, the hypovolemic range and the range are correlated to IVC diameter or volume measurements for the patient, identifying a hypovolemic warning zone for the patient encompassing a portion of the defined euvolemic region at a lower end of the euvolemic region adjacent the hypovolemic region, identifying a hypervolemic warning zone for the patient encompassing a portion of the defined euvolemic region at an upper end of the euvolemic region adjacent the hypervolemic region, generating an alert signal when measured IVC diameter or volume falls within either of the hypovolemic warning zone or hypervolemic warning zone of the defined euvolemic region before the patient fluid state reaches one of the hypovolemic region or hypervolemic region, respectively.

In some embodiments the wireless sensing device may comprise an ultrasound transducer and anchor element configured to anchor the ultrasound transducer in the IVC in a fixed position relative to the IVC wall. In other embodiments, the wireless sensing device may comprise a resilient coil forming a resonant circuit, wherein the resilient coil is configured to engage the wall of the IVC and deform therewith to provide a variable characteristic frequency correlated to an IVC physical dimension in response to activation of the resonant circuit. Such a system may further include an antenna configured to activate the resonant circuit and receive the signal representative of the measured IVC physical dimension in response to activation.

Further alternative embodiments disclosed herein include methods of managing patient body fluid volume. One embodiment of the disclosed methods may include directly measuring a physical dimension of the patient's IVC with a sensing device implanted within the IVC, wirelessly communicating with the implanted sensing device to monitor changes in the measured IVC dimension throughout an euvolemic region defined for said patient, and generating an alert signal when measured IVC diameter or area approaches or falls outside predetermined clinical limits for the patient. The alert signal may be direct to a healthcare provider or to the patient. When directed to the patient, the alert signal may include a prompt to initiate a patient self-directed treatment.

In some embodiments the predetermined clinical limits may include at least a first, lower limit indicative of the patient fluid state trending towards hypovolemia, and a second, higher limit indicative of the patient fluid state trending towards hypervolemia. Further, each of the predetermined limits falls within the euvolemic range defined for the patient. In such embodiments, further method steps may comprise setting (1) a hypovolemic warning zone for the patient encompassing a portion of the defined euvolemic region at the lower end of the euvolemic region adjacent a hypovolemic region and (2) a hypervolemic warning zone for the patient encompassing a portion of the defined euvolemic region at the upper end of the euvolemic region adjacent a hypervolemic region, wherein the euvolemic range, hypovolemic range and hypervolemic range are correlated to IVC physical dimension measurements for the patient.

In another alternative embodiment disclosed herein, a diagnostic method for monitoring patient body fluid volume comprises positioning a sensing device within the patient's IVC, wherein the sensing device is configured to measure at least one physical dimension of the IVC. Wirelessly monitoring changes in measured IVC physical dimension over time throughout an euvolemic region defined for said patient. Identifying (1) a hypovolemic warning zone for the patient encompassing a portion of the defined euvolemic region at the lower end of the euvolemic region adjacent a hypovolemic region and (2) a hypervolemic warning zone for the patient encompassing a portion of the defined euvolemic region at the upper end of the euvolemic region adjacent a hypervolemic region, wherein the euvolemic range, hypovolemic range and hypervolemic range are correlated to IVC physical dimension measurements for the patient. Another step in such a method as disclosed may include signaling a warning state when measured IVC physical dimension falls within either of the hypovolemic warning zone or hypervolemic warning zone of the defined euvolemic region before the patient fluid state reaches one of the hypovolemic region or hypervolemic region, respectively.

BRIEF DESCRIPTION OF THE DRAWINGS

For the purpose of illustrating the disclosed embodiments, the drawings show aspects thereof. It is to be understood, however, that the teachings of the present disclosure are not limited to the precise arrangements and instrumentalities shown in the drawings, wherein:

FIG. 6C shows examples of screen shots from a patient's mobile device presenting patient prompts as part of a patient self-directed therapy algorithm.

FIGS. 12A, 12B, and 12C illustrate more details of further embodiments of IVC measurement implants according to the present disclosure.

DESCRIPTION OF EMBODIMENTS

Embodiments disclosed herein include systems and methodologies allowing for regular, periodic or continuous monitoring of fluid volume more accurately than current techniques and with reduced lag time before changes in volume status are observed, thus providing earlier warning of hypervolemia or hypovolemia and enabling the modulation of patient treatments to permit more stable long term fluid management. Further, in acute situations, the methods and systems disclosed enable more rapid reduction of excessive intravascular volume and edema and restoration of more ideal fluid balance, with lessened risk of creating a hypovolemic state as can be created when patient "drying" treatments overshoot due to the response of patient monitoring devices or protocols.

A challenge presented by patients in decompensated heart failure is managing patient fluid balance, bringing down excess fluid volume as quickly as possible, but without overshooting and taking the patient into a potentially equally dangerous hypovolemic state. In the longer term management of heart failure, maintaining fluid balance is still a challenge, but in this case it involves maintaining the patient well within a safe fluid state without unintentionally migrating into a hypervolemic or hypovolemic state.

Figure 1:
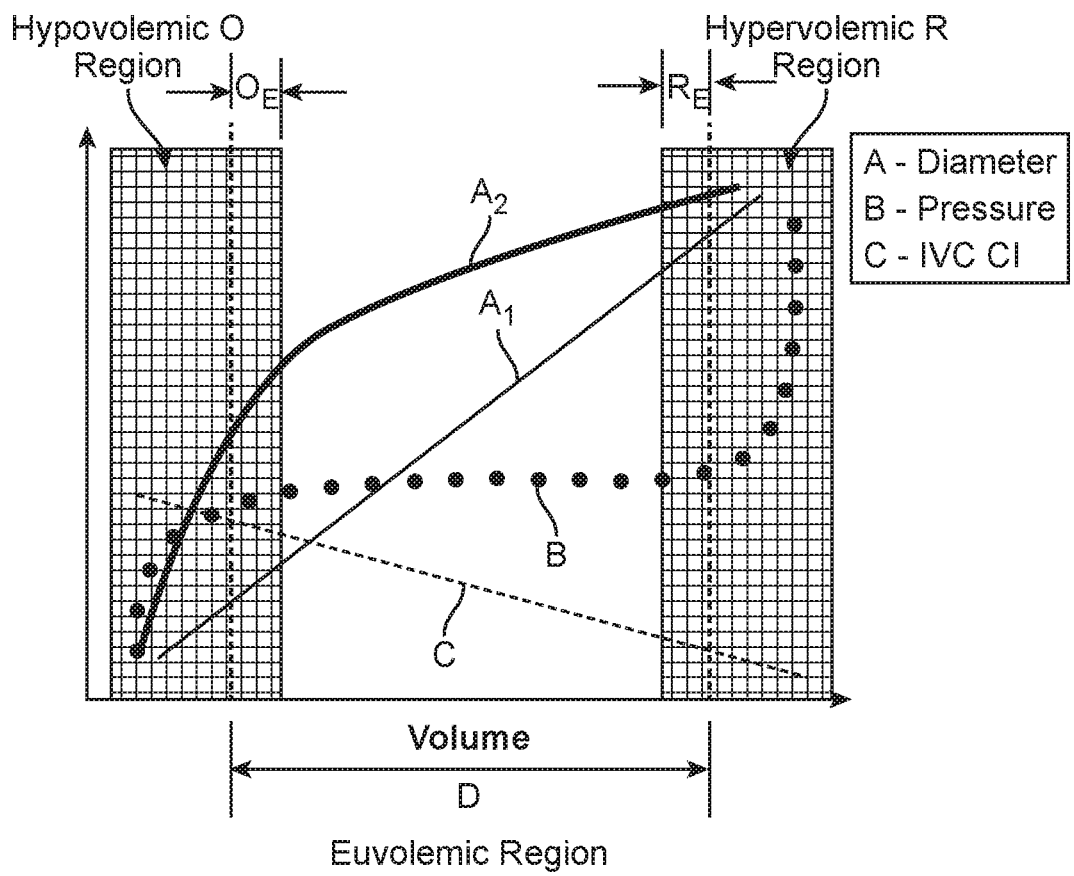
FIG. 1 is a schematic plot of patient fluid volume versus response for disclosed embodiments employing on IVC diameter or area measurement (curves $A_1$ and $A_2$) in comparison to prior pressure-based systems (curve B) and in general relationship to IVC collapsibility index (IVC CI, curve C).

Existing clinical devices focused on pressure measurement present certain difficulties in meeting these challenges. Pressure measurements can be useful as an indicator of gross fluid volume change, and as a predictor of acute decompensation when fluid levels are already at a relatively high level. However, detectable changes in PAP can lag changes in physiological state to an extent that a patient may be in an early stage of the risk zone before the change is identified. Also, as shown in FIG. 1, the relationship between pressure and volume in the IVC is highly nonlinear over the entire range from hypovolemic to euvolemic to hypervolemic, exhibiting significant volume change within the mid-range, generally euvolemic state, with minimal corresponding change in pressure that can be measured. (See FIG. 1, curve B). For these reasons, PAP and CVP can be limited predictors of volume status and likelihood of acute decompensation before a near acute stage is reached.

While there is a general knowledge of a correlation between IVC diameter and patient health and fluid state, existing devices and techniques for monitoring patient fluid state across the full volume range have not led to treatment systems or methodologies permitting more rapid stabilization of acute patients and longer term maintenance without that avoids the critical fluid states and may thus lead to otherwise unnecessary treatments or hospitalizations.

"Euvolemia" refers to the normal fluid volume in a patient's body, and "euvolemic region" refers to a range of fluid volume within the patient that is clinically characterizable as normal or not requiring intervention. ("Euvolemia" is also sometimes referred to in the medical literature as "normovolemia.") The euvolemic region, as explained in more detail below, also a fluid state or volume range across which measurement of central venous pressure (CVP) in the IVC is generally non-responsive to changes in fluid volume. "Hypervolemia" refers to a state in which a patient's body fluid volume exceeds a normal range, and "hypervolemic range" refers to a range of fluid volume within the patient that is clinically characterizable as excessive. Intervention may be indicated when a patient trends towards, enters into or persists within the hypervolemic range. "Hypovolemia" refers to a state in which a patient's body fluid volume is below a normal range, and "hypovolemic range" refers to a range of fluid volume within the patient that is clinically characterizable as insufficient. As with the hypervolemic range, intervention also may be indicated when a patient trends towards, enters into or persists within the hypovolemic range. As is well-understood by clinicians and other persons of skill in the art, these body fluid states are not static nor are they uniform or in terms of absolute volume. While it is possible for a person of ordinary skill to assign approximate ranges of parameters generally corresponding to the different fluid states, it can be difficult in practice for ordinary skilled persons, with existing diagnostic tools and methods, to identify where a particular patient's fluid state may reside with respect to the euvolemic, hypovolemic and hypervolemic ranges.

In response to the need for more accurate devices with faster response times, the Assignee of the present disclosure has developed a number of new devices that provide fluid volume data based on direct measurement of physical dimensions of the IVC, such as the diameter or area. Examples of these new devices are described, for example, in PCT/US2016/017902, filed Feb. 12, 2016, U.S. Provisional Patent Application, Ser. No. 62/427,631, filed Nov. 29, 2016, and U.S. Provisional Application, Ser. No. 62/534,329, filed Jul. 19, 2017 by the present Applicant, each of which is incorporated by reference herein in its entirety. Devices of the types described in these prior disclosures facilitate new management and treatment techniques as described herein based on regular intermittent (e.g., daily) or substantially continuous (near real-time), direct feedback on IVC diameter.

In further alternative embodiments disclosed herein, patient fluid state can be further modulated based on a combination of IVC data with other monitoring signals; symptoms and clinical input, by use of IVC data as it is influenced by some stimulus (e.g., exercise; leg raises) to indicate either system capacitance or redistribution of fluid, by use of IVC measurements from an implanted sensor to transmit regular information locally to help the clinical management of patients, e.g. patients managing their own dialysis and/or diuresis at home, or by use of IVC measurement from an implanted sensor to control drug delivery (e.g., like a closed loop implanted system for diabetes). Advantages achievable with disclosed systems and methods may include improved reduction of excessive intravascular blood volume in the clinical setting, through the controlled use of diuretics, more accurate management of blood volume in the home setting, through the monitoring of patients and use of a treatment algorithm, more rapid dialysis through the monitoring of volume and informed variation of dialysis rate.

As an illustration of the presently disclosed methodology, FIG. 1 presents a schematic plot of patient fluid volume versus a number of responses. IVC diameter or measurement versus Volume are shown by curves $A_1$ and $A_2$ in comparison to IVC Pressure versus Volume (curve B) and the IVC collapsibility index versus Volume (IVC CI, curve C). The IVC collapsibility index (CI) is equal to the measured IVC dimension at maximum extension minus the same dimension at minimum extension divided by the maximum extension dimension. (CI=Max−Min/Max). Any single dimension measurement may be used, i.e. major diameter, minor diameter or area (see FIG. 7). It should be noted that FIG. 1 is intended only to summarize and illustrate overall relationships of the parameters discussed, and does not represent specific data points or data plotted to scale. (Curves A1 and A2 represent data from preclinical and benchtop testing conducted by the present Applicant based on prototype devices of a type described herein. Curve B is adapted from canine IVC results published by Moreno et al., Circ. Res. (1970) 27 (5): 1069-1080.

As can be seen in FIG. 1, the response of pressure-based diagnostic tools (B) over the euvolemic region (D) is relatively flat and thus provides minimal information as to exactly where patient fluid volume resides within that region. Pressure-based diagnostic tools thus tend to only indicate measureable response after the patient's fluid state has entered into the hypovolemic region (0) or the hypervolemic region (R). In contrast, a diagnostic approach based on IVC diameter or area measurement across the respiratory and/or cardiac cycles ($A_1$ and $A_2$), which correlates directly to IVC volume and IVC CI (hereinafter "IVC Volume Metrics") provides relatively consistent information on patient fluid state across the full range of states.

Using IVC diameter or area measurement as an indicator of patient fluid volume as disclosed herein thus provides an opportunity for earlier response both as a hypovolemic warning and as an earlier hypervolemic warning. With respect to hypovolemia, when using pressure as a monitoring tool, a high pressure threshold can act as a potential sign of congestion, however when pressure is below a pressure threshold (i.e., along the flat part of curve B), it gives no information about the fluid status as the patient approaches hypovolemia. With respect to hypervolemia, IVC diameter or area measurements potentially provide an earlier signal than pressure-based signals due to the fact that IVC diameter or area measurements change a relatively large amount without significant change in pressure. Hence, a threshold set on IVC diameter or area measurements can give an earlier indication of hypervolemia, in advance of a pressure-based signal.

Based on systems and methods disclosed herein, a patient healthcare provider can devise defined early warning zones for the hypovolemic region ($O_E$) and hypervolemic region ($R_E$). Just as the euvolemic region boundaries vary from patient to patient based on many physical and health related factors, such as age, sex, obesity and disease state. The early warning zones reside within the euvolemic range immediately adjacent the hypovolemic and hypervolemic regions such that the patient may still be considered to be within acceptable fluid balance parameters when in the early warning zones. However, the ability to define early warning zones as such based on IVC diameter or area measurements means that appropriate interventions may be initiated earlier, before the patient reaches higher levels of criticality, and thus also may be controlled more precisely and smoothly to minimize risk of shock from sudden interventions and/or overshoot of therapy targets. Table II below illustrates an example of possible fluid state regions for a hypothetical patient in accordance with the teachings of the present disclosure.

TABLE I

Example of Fluid State Regions for Hypothetical Patient

| Hypovolemic Region (O) | Hypovolemic Early Warning Zone ($O_E$) | Euvolemic Region | Hypervolemic Early Warning Zone ($R_E$) | Hypervolemic Range (R) |
|---|---|---|---|---|
| IVC Ø <14 mm + IVCCI >75% | IVC Ø = 14-16 mm + IVCCI = 60-75% | IVC Ø ~ 14-21 mm + IVCCI ~ 50-75% | IVC Ø = 19-21 mm + IVCCI = 50-60% | IVC Ø >21 mm + IVCCI <50% |

Figure 2:
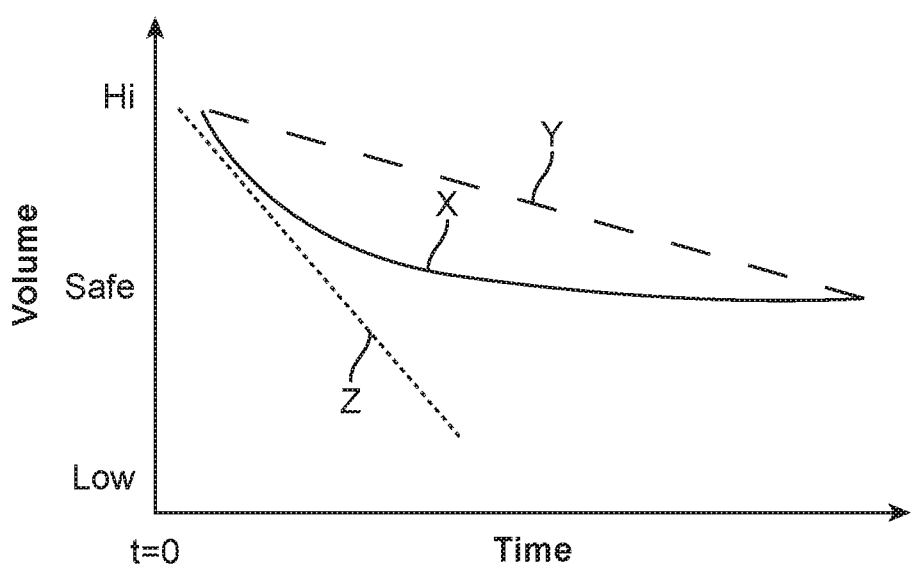
FIG. 2 illustrates a hypothetical comparison of patient fluid volume over time in treatment for hypervolemia as between an IVC diameter or area measurement-based approach according to the present disclosure (curve X) and a typical pressure-based approach (curves Y and Z).

FIG. 2 illustrates a hypothetical comparison of patient fluid volume over time in treatment for hypervolemia as between an IVC Volume Metrics-based approach according to the present disclosure (curve X) and a typical pressure-based approach (curve Y). Because of the greater information available in the euvolemic region, the IVC Volume Metrics-based approach permits more aggressive initial treatment with lower risk of overshoot into the hypovolemic region (low), resulting in bringing the patient into the euvolemic region (safe) more quickly as compared to a pressure-based system, which must modulate therapy more gradually. Curve Z illustrates the potential risk for a pressure-based system if treatment were initially applied in a manner similar to the IVC Volume Metrics-based system. Without the greater information and feedback available (as illustrated by FIG. 1, curves $A_1$ and $A_2$), by the time the treatment provider sees a response from the diagnostic tools, the aggressive treatment may have already pushed the patient into the hypovolemic region (low).

Figure 3A:
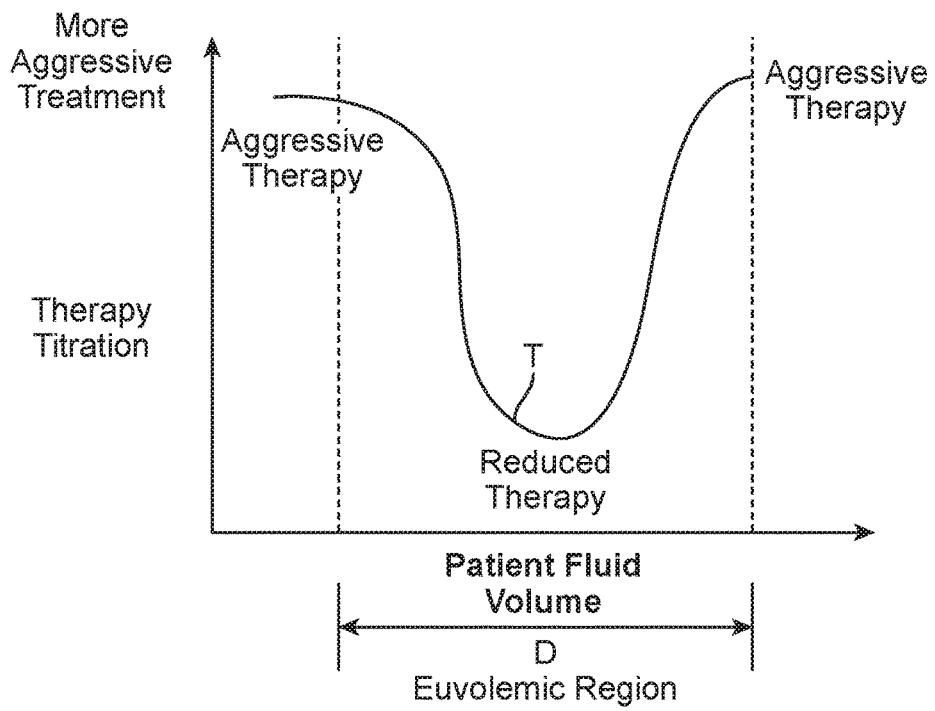
FIGS. 3A and 3B schematically illustrate alternative treatment embodiments employing titration of therapy based on disclosed systems.
Figure 3B:
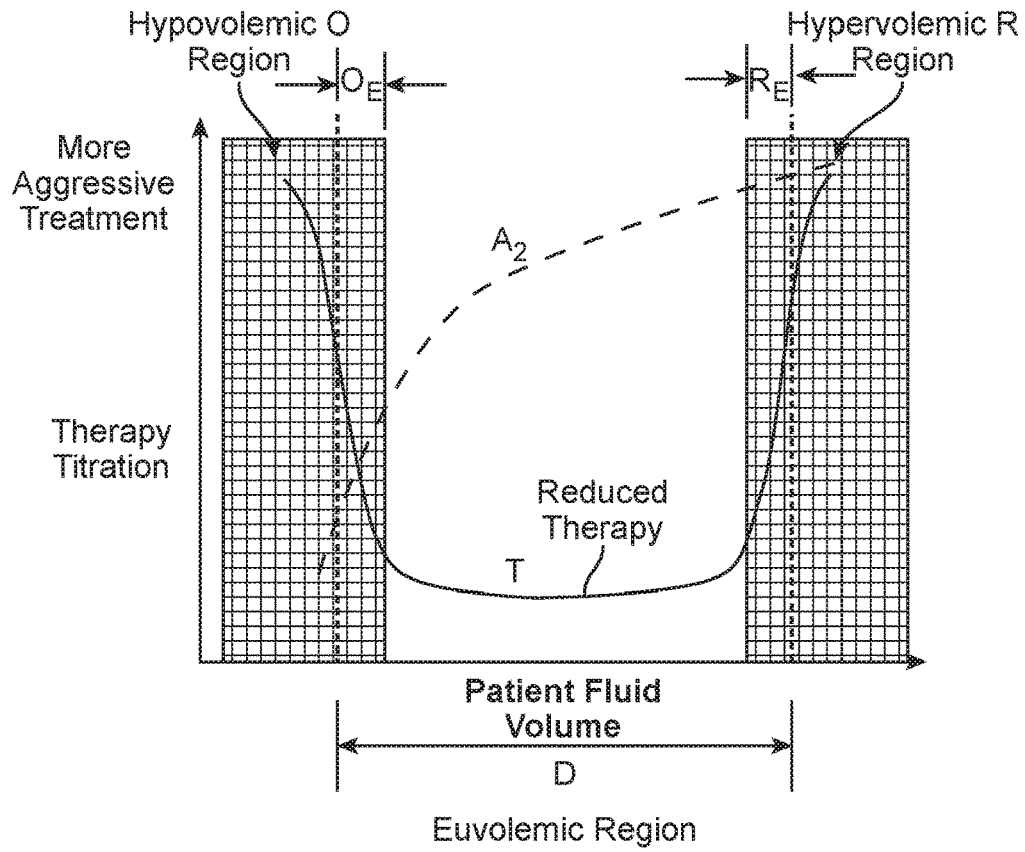

Use of IVC diameter or area measurements as described herein thus offers advantages in titrating patient therapies. FIGS. 3A and 3B illustrate embodiments of possible therapy titration schedules over the patient fluid state ranges based on the teachings of the present disclosure. Because IVC diameter/area changes more accurately reflect changes in patient fluid volume consistent with actual fluid state, IVC diameter or area measurements can be used to help titrate treatments more precisely and adjust the therapeutic intervention more subtly and incrementally, rather than just using a hard threshold as is now the clinical norm. Use of IVC diameter or area measurements also allows the flexibility of potentially titrating patients to a personalised volume, for example, keeping a patient with reduced cardiac ejection fraction (HFrEF) at a wetter point, while maintaining a patient with preserved cardiac ejection fraction (HFpEF) at a drier point.

FIG. 3A describes one possible treatment algorithm in this regard in which patient therapy is reduced when the patient's flood volume comfortably falls in the mid-range of the euvolemic region. In this treatment algorithm example, in which curve (T) represents a relative therapy level plotted against patient fluid volume, therapy is increased relatively rapidly once the patient's fluid volume moves from the mid-range of the euvolemic region as indicated by monitored changes in the IVC diameter or area. Such a treatment algorithm may be appropriate, for example, for a patient that is known to have a slow response to therapy in order to avoid having the patient move too far into the hypovolemic or hypervolemic regions before responding to the treatment. FIG. 3B describes another possible treatment algorithm based on the teachings of the present disclosure. In this example, relative therapy curve (T) is flatter across the majority of the euvolemic region (D) and only significantly increases once fluid volume, as determined based on sensed changes in IVC diameter or area, moves into one of the predefined early warning regions $O_E$ or $R_E$ that have been determined to be clinically appropriate for the specific patient being monitored. For illustration purposes, curve $A_2$ from FIG. 1 (representing change in IVC diameter/area vs. fluid volume) is superimposed over treatment curve (T) in FIG. 3B so that the relative relationship between IVC diameter/area change and treatment algorithm in this example may be better appreciated.

Figure 3C:
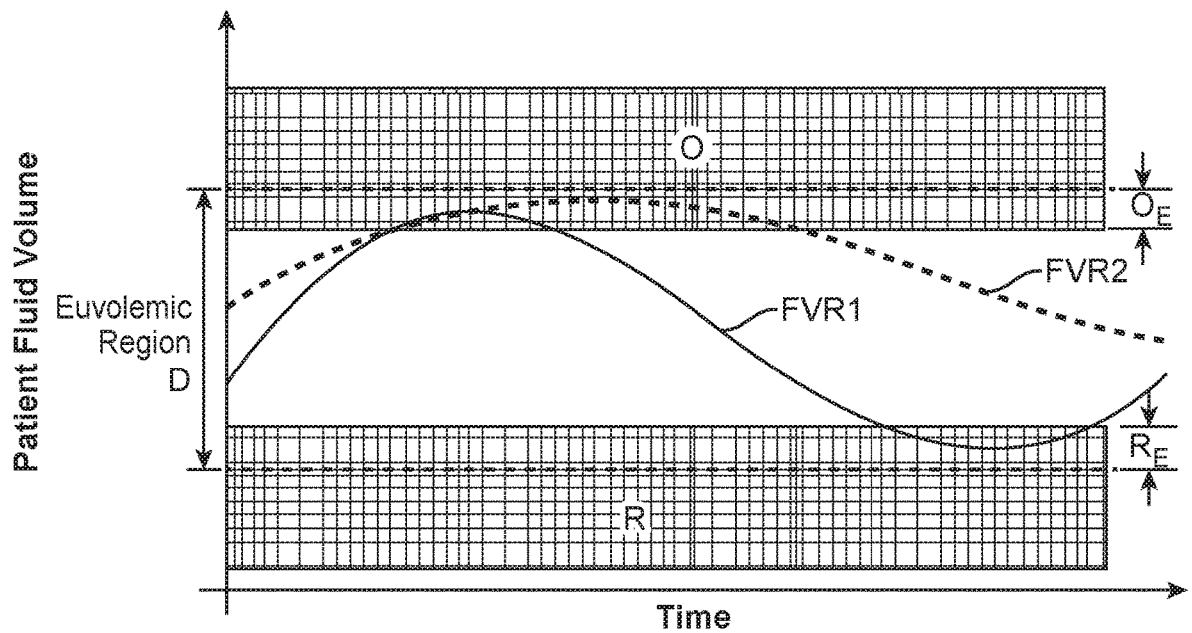
FIG. 3C illustrates a treatment scenario based on disclosed system embodiments.

FIG. 3C schematically illustrates practical application of the relationships illustrated in FIG. 1 and potential advantages of treatment algorithms such as described in FIGS. 3A and 3B, based on sensed changes in IVC diameter or area as disclosed herein. In FIG. 3C, relative patient fluid volumes for hypothetical patients (whose therapy is titrated according to a treatment algorithm as described above) are plotted against relative time. Curves FVR1 and FVR2 thus represent two hypothetical examples of patient fluid volume response to therapy over time. In each case, applying a treatment algorithm such as described in the examples of FIG. 3A or 3B, patient therapy can be titrated more accurately with respect to actual fluid state within the euvolemic region such that therapy may be applied at appropriate times earlier and more gradually to ensure that overall patient fluid volume stays within or as close as possible to the euvolemic region.

IVC diameter or area measurements also may be used in combination with other diagnostic signals to provide guidance on therapeutic intervention, e.g. diuretics versus vasodilators. When used with intervention, the IVC diameter or area measurement time dynamics response may be used to give information on the fluid status/distribution of the patient to guide therapy intervention. Response of IVC diameter or area measurements to a perturbation, e.g., physical activity, can cause sympathetic nerve response and fluid redistribution. Looking at changes in IVC diameter or area will thus provide information on fluid volume status. In other words, an act as simple as a leg raise may cause a fluid change/redistribution that could also provide information on fluid volume status that would not be visible with pressure-based systems. Thus, in certain embodiments, at-risk patients may have continuous or near-continuous monitoring of IVC diameter or area changes during physical activity.

Sensed changes in IVC diameter or area also may be combined with other parameters such as with BNP or pressure/edema signals to help guide therapy intervention or differentiate patient phenotype (HFrEF v HFpEF). Examples include detection of low collapsibility plus peripheral edema as an indication for diuretic therapy or detection of low collapsibility without peripheral edema as an indication for indicate vasodilator therapy. Combination of monitoring IVC diameter or area changes with implanted pressure-based monitors (in the IVC, right atrium, right ventricle, pulmonary artery, left atrium, or other vessel) also may permit determination of abdominal pressure and flow in the IVC. In addition, the IVC monitoring device of the invention may include additional sensors to measure non-dimensional parameters within the IVC such as blood flow rate and venous pressure. Further, measurement of the dimensions or non-dimensional parameters of other vessels, such as the superior vena cava, pulmonary artery, or heart chambers, may in some cases be advantageous to supplement IVC measurement. In such cases, dimensional measurement devices similar to the IVC monitoring device of the present invention may be configured for implantation in such other vessels. In such embodiments, the methods and systems of the invention may be adapted to receive such supplementary data from these sources and incorporate such data in the determination of fluid status, heart failure status, appropriate thresholds for communicating alerts or messages, or therapeutic treatment plans or recommendations.

Figure 4A:
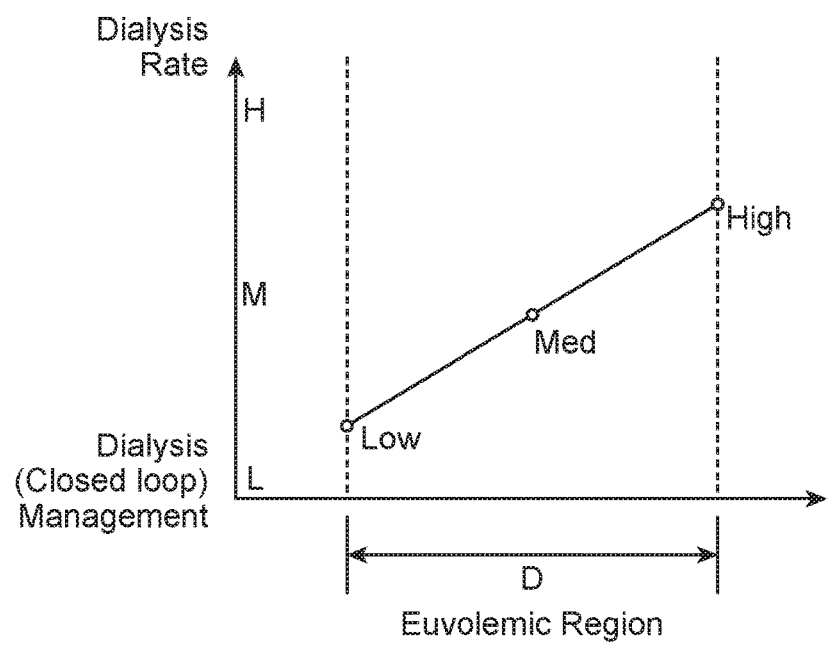
FIGS. 4A, 4B, 4C, 5A and 5B schematically illustrate embodiments of closed loop control of dialysis and therapy/treatment devices based on systems disclosed herein.

Use of IVC diameter or area measurements also leads to the development of new systems such as closed-loop systems for therapy intervention as described herein. Examples include modification of a standard dialysis system filtration rate from a constant rate to a faster or variable rate using information that was previously unavailable to the clinician or patient. In one example, as illustrated in FIG. 4A, IVC diameter or area measurements may provide faster dialysis treatment in a closed-loop system, such as described below, by guiding higher filtration rates while the fluid load is high and inform reducing filtration rate as the fluid is reduced, ultimately resulting in a faster and safer treatment. Hypotensive events may occur in patients undergoing dialysis due to fluid removal occurring too rapidly. FIG. 4A plots patient fluid volume against rate of dialysis for a closed-loop system based on embodiments described herein, which may allow for more efficient dialysis, e.g., fast enough to remove fluid without the side effects of fast fluid removal. When ultra-filtration (UF) is constant, the degree of vascular refilling will differ from patient to patient, therefore using additional information provided by IVC diameter or area measurements may allow the UF rate to be more accurately individualized in a time dependent fashion over the course of the dialysis session for specific patients. IVC diameter or area measurement information may be combined with other diagnostic tools such as blood pressure monitoring to more accurately estimate fluid volume status as a basis for altering the rate of filtration.

Figure 4B:
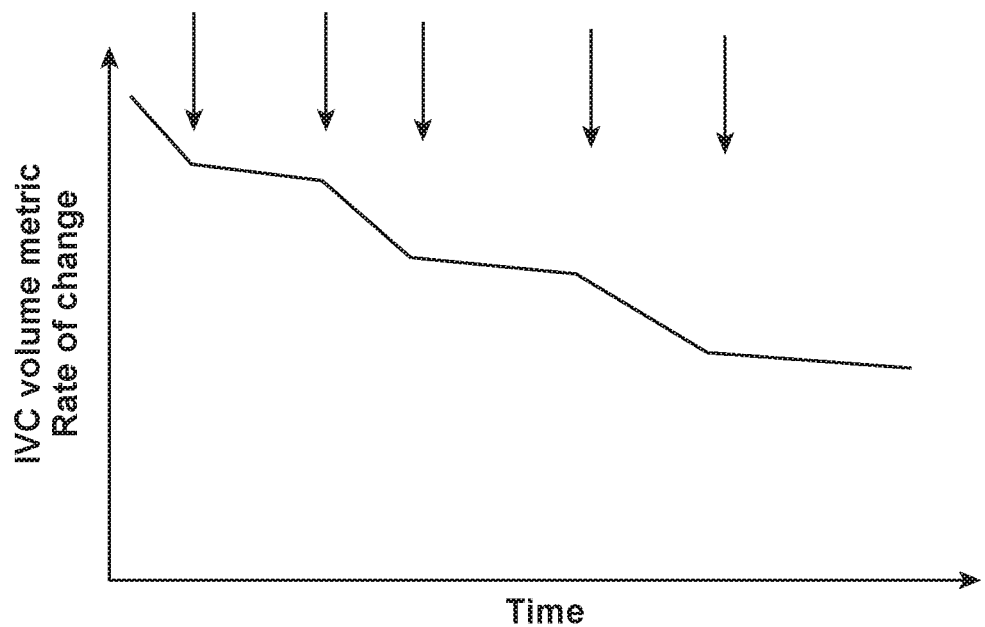
Figure 4C:
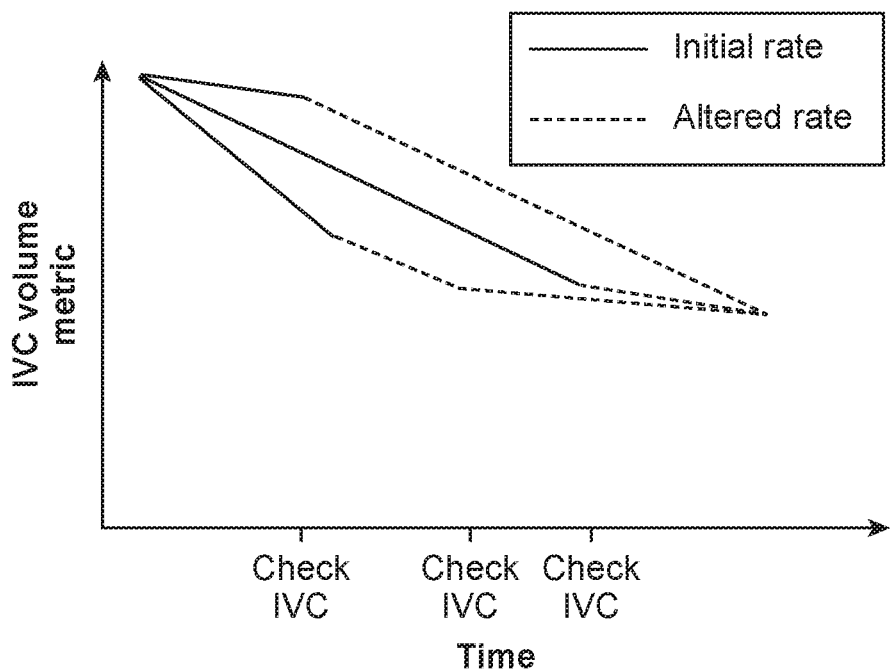

FIG. 4B illustrates another embodiment in which alteration of dialysis filtration rate may be based on periodic assessments of IVC diameter or area change, e.g., a percent change in IVC volume metric per hour coinciding with a total desired volume that needs to be removed. (Each downward arrow in FIG. 4B indicates relative time of each assessment.) This is another alternative approach to control of UF rate, which allows increased accuracy and individualization of treatment for specific patients in a time dependent fashion over the course of a dialysis session. Another alternative dialysis control methodology is described in FIG. 4C in which the IVC volume metric rate of change, based on measured changes in IVC diameter or area, is plotted against time through a hypothetical dialysis session. Employing systems as described herein, time-based check points may be provided, at which time the measured IVC volume metric is checked against predefined patient specific targets. At each check point, UF rate may be altered as needed to direct the patient more efficiently and smoothly to the final fluid volume target. Compared to existing systems, which rely primarily on dry weight estimation based on inter-dialytic weight gain, employing methodologies as described in any of FIGS. 4A, 4B and 4C with systems disclosed herein provides for increased individualization of UF rate for specific patients over the course of the dialysis session.

Figure 5A:
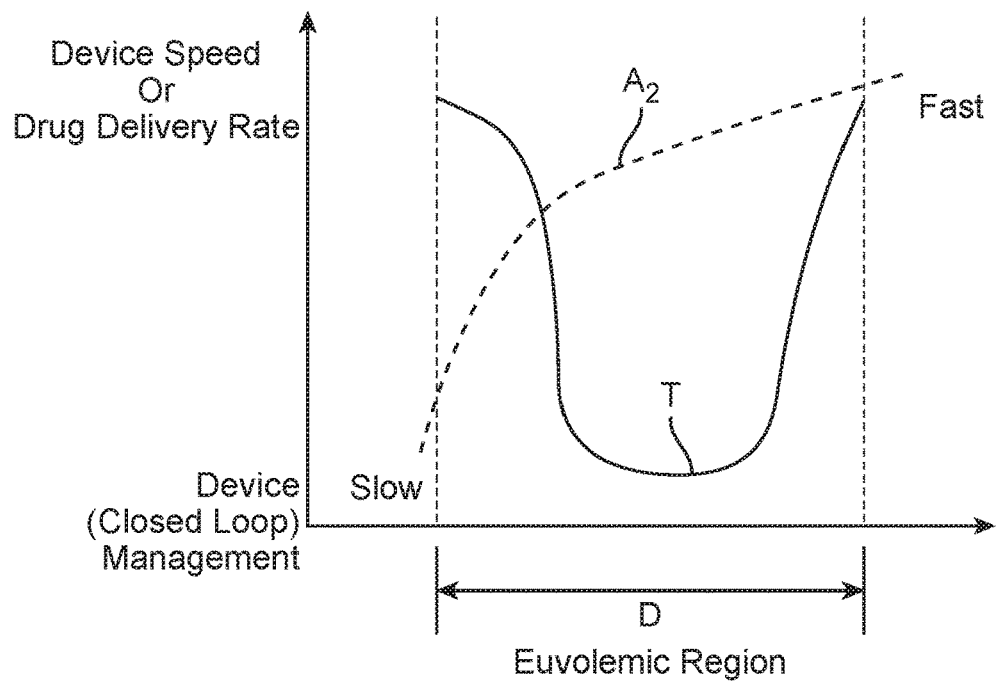
Figure 5B:
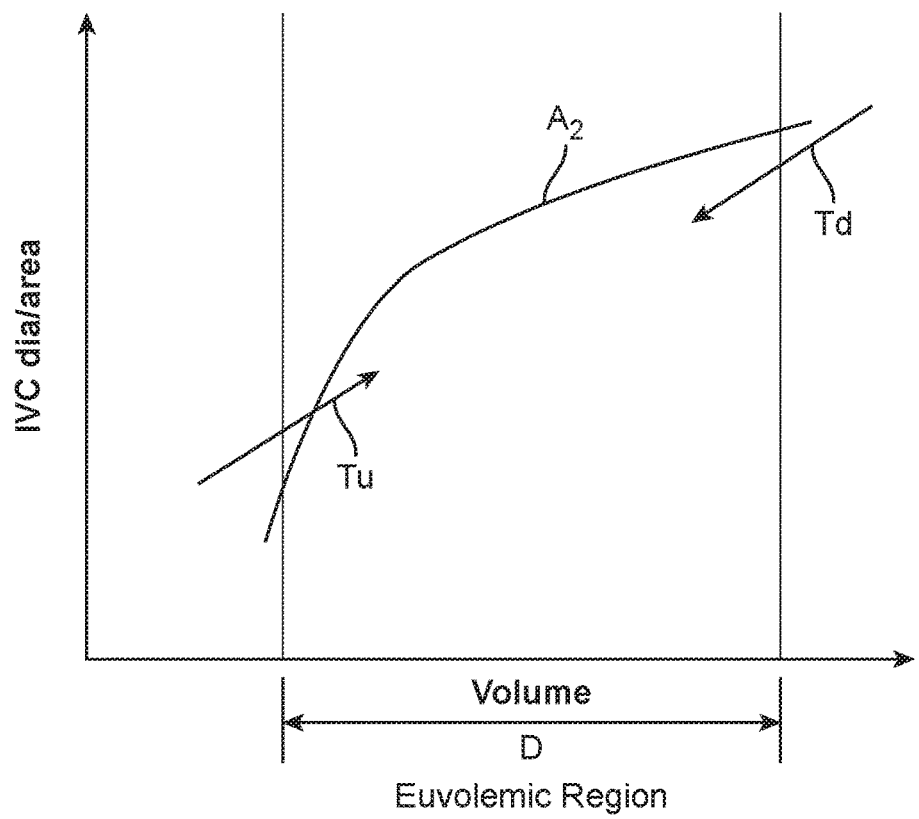

In another example, illustrated in FIG. 5A, an implanted drug pump or device may be provided, for example as a closed-loop dialysis management system. In such a system, at a hypervolemic end of the scale the device runs at high speed/delivers large load. As volume is reduced the device slows. This allows time for the interstitial fluid to return to the intravascular space. As the fluid load approaches hypovolemia the device speed/drug load rate could increase proportionally to avoid a hypovolemic state. Such control requires knowledge of incremental changes in fluid state across the euvolemic ranges, which is provided by methodologies and systems described herein. As a point of reference, curve A2 indicating relative IVC diameter or area measurement (from FIG. 1) is superimposed on the treatment curve (T) in FIG. 5A. In yet a further example, illustrated in FIG. 5B, a closed loop system according to embodiments described herein allows for volume control-based therapy delivery modulated based on measured changes in IVC diameter or area. In this example, at either end of the euvolemic region (D), therapy delivery, e.g., drug delivery such as a diuretic or dialysis filtration, may be altered up ($T_u$) or alerted down ($T_d$) in accordance with IVC diameter or area measurements.

Figure 6A:
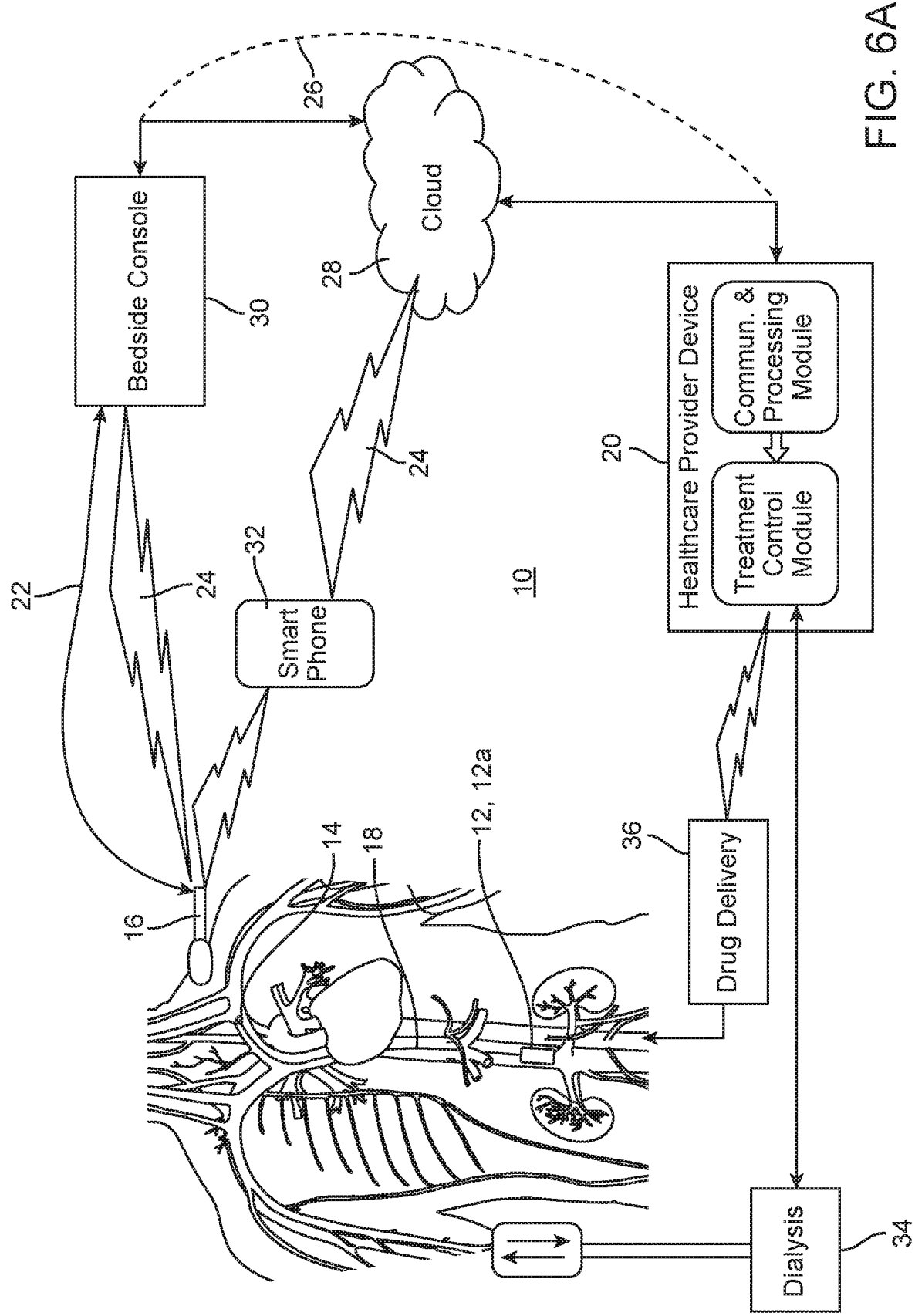
FIGS. 6A and 6B schematically depict components and possible arrangement of alternative system embodiments as disclosed herein.

FIG. 6A schematically illustrates one exemplary system 10 including an IVC diameter/area measurement monitoring device 12 positioned at a monitoring location in the IVC. In the example illustrated, monitoring device 12 is an ultrasound-based device 12a anchored within the IVC and uses an ultrasound signal reflected off the opposite wall of the IVC to detect the distance by measuring the time-of-travel of this signal and thus provide a diameter measurement. Other examples of monitoring devices include resonant circuit-based devices in which characteristic inductance varies as the devices expand or contract with the IVC wall. Non-limiting examples of monitoring devices that may be used in systems according to the present disclosure are described below and shown in FIGS. 10, 11, and 12A-C. Further examples and details of suitable IVC diameter/area monitoring devices are disclosed in the aforementioned and incorporated PCT and provisional applications by the present Applicant.

Measurements of IVC diameter or area by monitoring device 12 may be made continuously over one or more respiratory cycles to determine the variation in IVC dimensions over this cycle. Further, these measurement periods may be taken continuously, at preselected periods and/or in response to a remotely provided prompt from a health care provider/patient. In this example, monitoring device 12 may communicate via an implanted antenna 14 positioned in the left brachiocephalic vein or other location close to an insertion point or location facilitating signal detection by an external antenna or detector 16. External antenna/detector 16 may be configured to be handheld by the patient or healthcare provider, or worn by or affixed to the patient in an anatomical location selected for optimal communication with the implanted antenna 14. Communication between the implanted antenna 14 and monitoring device 12 occurs via an intravascular lead 18, which extends through the venous vasculature to the monitoring device 12. This is just one example of a communications arrangement with a monitoring device such as device 12. In another example, wireless communication to receiver(s) outside the body may be effected directly by the monitoring device itself, without a separate, implanted antenna and connecting intravascular lead.

External antenna/detector 16 may be configured to communicate via wireless or wired connection with bedside console 30, smart phone 32, or other external communication/control device. Data collected by the monitoring device may be communicated ultimately to a healthcare provider device 20 via wired 22 and/or wireless 24 communications and/or directly through hard wired links such as telephone or local area networks 26 or through Internet or cloud based systems 28. Communications may be facilitated by a bedside console 30 in a home or clinical treatment location or, particularly in the case of implanted monitoring devices, through a mobile device 32, such as a smart phone. Healthcare provider device 20 may be configured with appropriate user interface, processing and communications modules for data input and handling, communications and processing, as well as treatment and control modules, which may include treatment algorithms as described herein for determining treatment protocols based on collected IVC diameter or area measurements, and systems for automated remote control of treatment devices based on determined treatment protocols as elsewhere described herein. Examples of such treatment devices include, but are not limited to, dialysis machine 34 and drug delivery devices 36. Examples of treatments include, when measured dimensions fall within the hypovolemic warning zone, administration of fluids or vasoconstricting drugs, and when measured dimensions fall within the hypervolemic warning zone, dialysis or administration of diuretics or vasodilating drugs.

IVC physical dimension data and/or fluid volume state information derived therefrom may also be communicated directly to the patient themselves, along with therapy advice based on this data and using pre-determined algorithms/implanted medical devices. Communications protocols throughout the system may include bidirectional communications to permit a healthcare provider (or other appropriately trained operator at another point in the system) to alter overall monitoring protocols executed at the monitoring device or, for example, to request additional queries by the monitoring device outside the current operational protocol.

Other embodiments include systems for patient self-directed therapy, for example with IVC volume metrics data utilized directly by the patient with or without clinician overview, e.g., for self-administration of drugs or other therapies. Such systems may also be implemented for home dialysis and/or peritoneal dialysis. Wireless communication between the IVC monitor and the patient's cell phone or computer would allow continuous or periodic transmission of IVC data and the use of software applications to provide alarms or reminders, graphically present trends, suggest patient actions, drug dosage options, or treatment system settings, and allow communication with physicians.

Figure 6B:
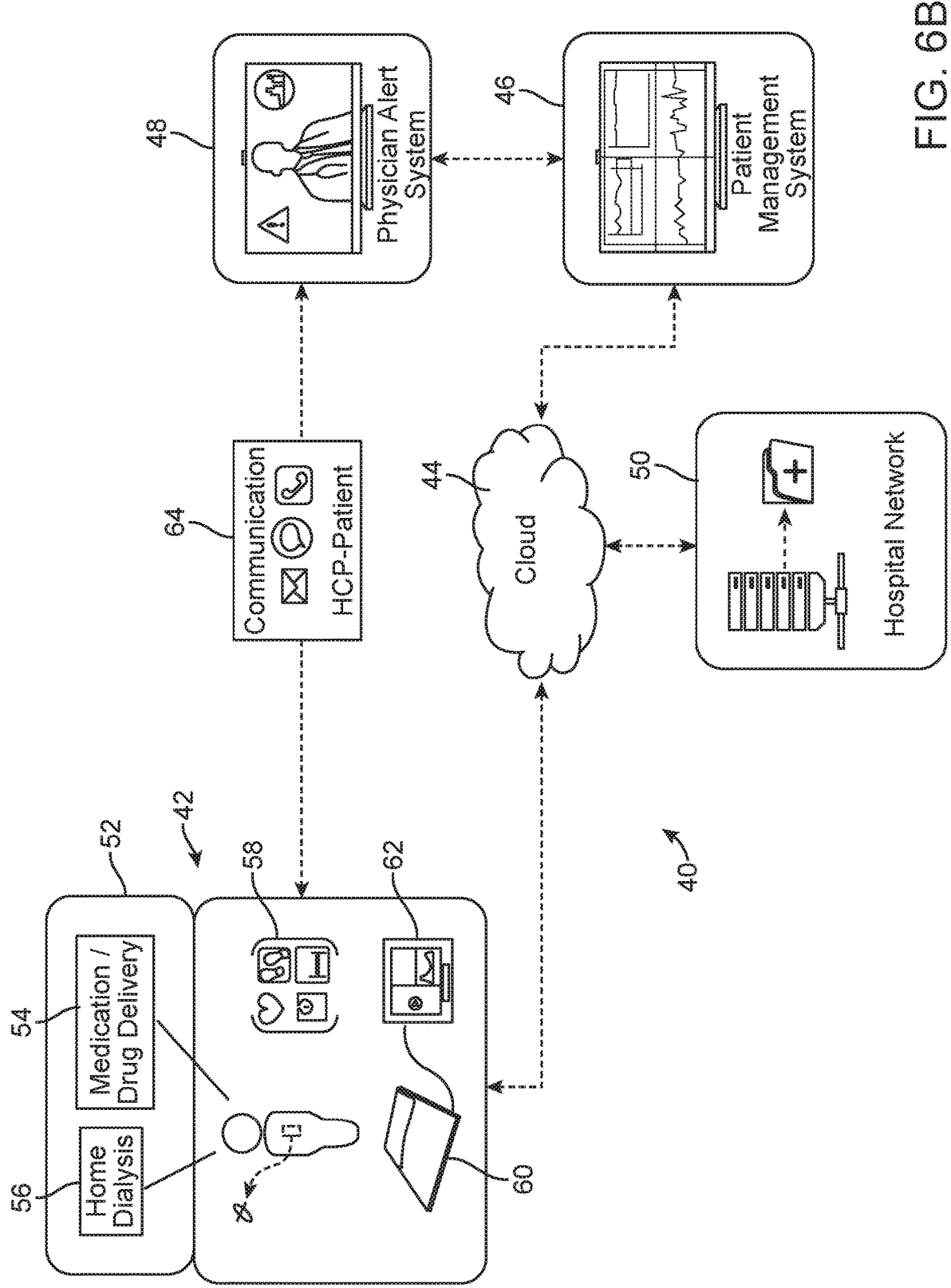

FIG. 6B schematically illustrates another exemplary system, which may, in one alternative, incorporate patient self-directed therapy. As shown in FIG. 6B, system 40 provides for communication between the patient home system 42, cloud storage 44, a patient management system 46, a physician alert system 48, and optionally a hospital network 50. Data transmission from the patient home system 42 to the cloud 44 for storage and access facilitates remote access for clinical and nursing teams. In patient self-directed therapy embodiments, patient's home may include home therapy devices 52, which may independently access cloud storage 44, and based on predetermined limits/treatment algorithms, indicate patient self-administration of medications or drug delivery 54 or home dialysis machines 56. In such a system a patient with wireless implant 12 may receive prompts from a cell phone or other device in the home at specific time intervals or in response to data 58 generated by other patient monitoring devices such as blood pressure, heart rate or respiration monitors that also communicate with the home device and may transmit data to cloud 44 for storage. System 40 may also include communication links (direct, networked or cloud-based) with such other monitoring devices to receive data 58 inputs used in setting warning zones and alert limits and assessing patient fluid state. Further inputs may be made by a user through a user interface, which may be, for example, configured as part of patient management system 46. User inputs may include additional patient-specific information such as patient age, sex, height, weight, activity level, or health history indicators.

In response to a prompt from system 40 to take a reading, the patient would position him/herself with respect to antenna/detector 60 as appropriate to communicate with selected implant 12. Antenna/detector 60 may communicate locally with a control console 62 to receive and interpret signals from implant 12. FIG. 6C shows screen shots of a patient mobile device with examples of sequential prompts as may be provided on a home/mobile/cellular device.

Varying levels of response may be generated by the home system 42 depending on IVC measurements received from implant 12 and as may be interpreted in light of other patient data 58. Minimal responses may indicate to the patient that fluid status is within acceptable ranges and no action is required. Mid-level responses may include prompts for medication administration or changes in home drug delivery, or home dialysis. Examples of treatment protocols are explained further below. When home dialysis or drug delivery is prompted, it may be controlled directly in a closed-loop system as described above or may be controlled by the patient with prompts from the system. Patient data 58 and IVC measurements from implant 12 also may be communicated continuously or periodically by system 40 to cloud storage 44 and further communicated to a remote patient management system 46. Functionality for system 40 may be largely contained in home system 42 or in patient management system 46 or appropriately distributed across the network. Optionally, patient related data including sensor results and patient health and fluid states also may be communicated to or accessible by a hospital network 60. System 40 also may receive patient related data, including for example, medical records related to past therapies and medical history.

When a patient condition is recognized by system 40 as outside acceptable limits, an alert may be generated by physician alert system 48. Information supporting the alert condition may be communicated, for example, through patient management system 46 to physician alert system 48. Physician alert system 48 may reside at a healthcare provider office or may include a mobile link accessible by the health care provider remotely, and which permits communication 64 between the healthcare provider and the patient. Communication 64 between healthcare provider and patient may be network, Internet or telephone based and may include email, SMS (text) messaging or telephone/voice communication. Physician alert system 48 allows the healthcare provider to review logs of IVC measurements over time and make decisions regarding therapy titration, and in critical cases, hospital admissions, remote from the patient.

Exemplary system embodiments 10 and 40 are each illustrated, respectively, in FIGS. 6A and 6B with various system functions assigned to particular functional elements of the systems. For the sake of clarity of the disclosure, not all possible distributions of functions in functional elements across the system are described. As will be appreciated by persons of ordinary skill, other than the function of the sensor implant itself and, in some instances, an antenna communicating wirelessly with the sensor implant, all functions may be distributed among functional elements in any number of arrangements as best suited to a home or clinical application and the intended location of sensor reading function, e.g., in a home or hospital setting. For example, all system functions (except sensor specific functions as mentioned) may be contained in a single functional unit in the form of a stand-alone patient management system. Alternatively, functions may be highly distributed among mobile devices networked with secure cloud computing solutions. For example, the sensor implant or, in cases where specific external antenna configuration is required, an antenna control module may communicate directly with a patient-owned smart phone to receive signals indicating IVC physical dimension measurements and, in turn, transmit those signals via WiFi or cell network to the cloud for distribution to further mobile devices in the possession of healthcare providers. Hand-held devices such as tablets or smart phones may communicate directly with controlled treatment delivery devices, or such devices may be controlled by a self-contained patient management system. Further, processing necessary for operation of the system also may be distributed or centralized as appropriate, or may be duplicated in multiple devices to provide safety and redundancy. As just one example, as shown in FIG. 6A, both bedside console 30 and smart phone 32 may be capable of performing identical functions and communicating with healthcare provider device 20 to report results of execution of the assigned functions. Thus, the specific arrangement of the functional elements (blocks) in the schematic presentations of the illustrative examples in FIGS. 6A and 6B are not to be considered as limiting with respect to possible arrangements for distribution of disclosed functions across a network.

Various care algorithms may be developed based on systems 10 and 40. In one scenario, a first, home-care algorithm governs interactions in the home system including periodic IVC diameter/area measurements using implant 12 and dictates whether to maintain current therapies or to change therapies within the scope of home-care team capabilities. As long as IVC volume metrics stay within predefined limits, the first, home-care algorithm continues to govern monitoring and treatment. However, if monitored parameters, for example IVC volume metrics, exceed the predefined limits, then an alert is generated that engages a second, healthcare provider algorithm. Such an alert may be generated internally by home system 42, or may be generated in patient management system 46 (or physician alert system 48) based on monitored data communicated by home system 42 and received by the other systems either periodically or on a continuous basis. In one embodiment, an alert initially is received by a physician's assistant or heart failure nurse who can triage the situation through patient management system 46. At that level the assistant or nurse may elect to generate a message for communication 64 to the patient through the network related to modulation of therapy or other parameters such as level of physical activity. However, if triage indicates the alert to represent a more critical event, the physician may be alerted through physician alert system 48. Multiple layers of care and review based on measured IVC volume metrics are thus provided to efficiently manage patient fluid status and where possible avoid hospitalizations.

Figure 7:
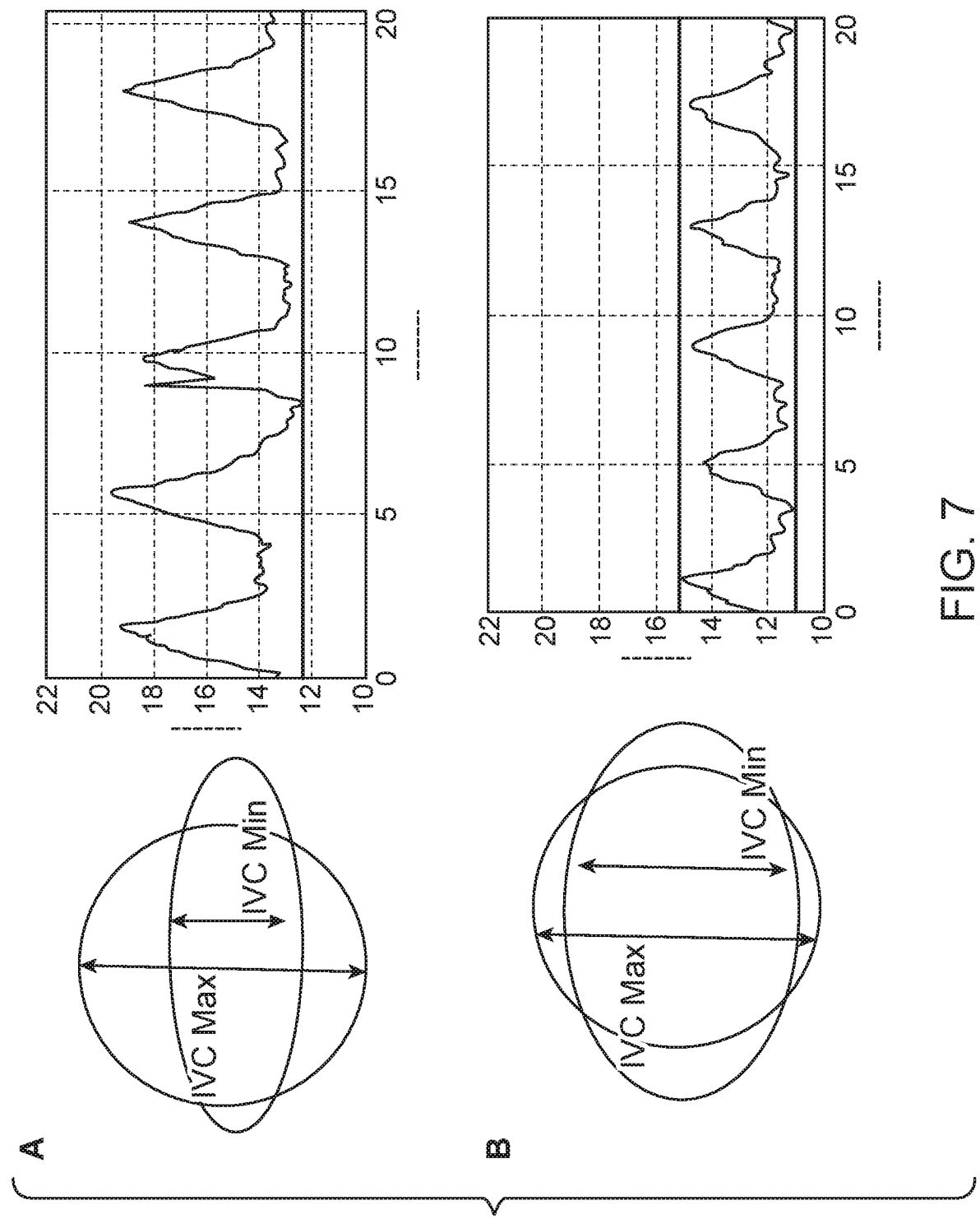
FIG. 7 illustrates an exemplary algorithm for determination of IVC collapsibility (IVC CI) on which a treatment algorithm may be based.
Figure 8:
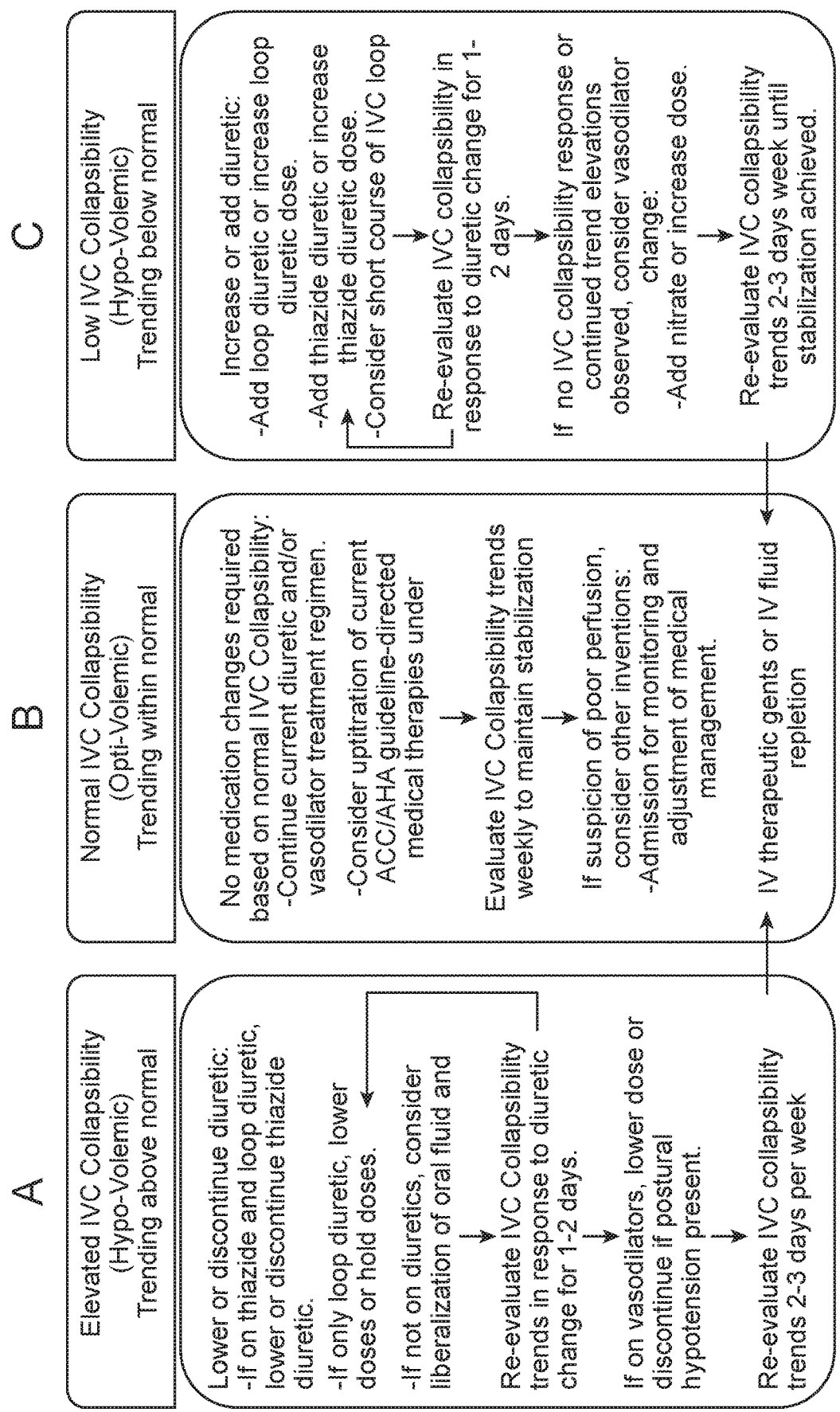
FIG. 8 illustrates a possible treatment algorithm according to the present disclosure.

As mentioned above, IVC collapsibility or IVC CI are parameters that may be generated to facilitate diagnostic decisions based on IVC metrics. FIG. 7 illustrates one exemplary algorithm for determination of IVC collapsibility on which a treatment algorithm may be based. One example of such a treatment algorithm is illustrated in FIG. 8. Another example is described below in Table I. Plots A and B in FIG. 7 show two different IVC collapsibility conditions plotted as diameter versus time over several respiratory cycles (in this case based on ultrasound detection, but diameter/area detection of the IVC may be based on any other modalities described herein to achieve similar results).

Based on a calculated IVC collapsibility, a treatment algorithm such as shown in FIG. 8 may be employed. Based on several published research studies, an IVC Collapsibility Index (IVC CI) of 15% or less indicates significant fluid overload, which may imply an imminent risk of acute decompensation. An IVC CI of 20-30% might be considered normal, and an IVC CI of greater than 40% might indicate a hypovolemic state. These percentages may be adjusted for patients with certain conditions. For example, a patient with heart failure with reduced ejection fraction might preferably be maintained at a lower IVC CI (i.e., with more circulating blood volume) to maximize cardiac output.

In developing any treatment algorithm a starting point is existing clinical guidelines, which a physician may then customize to an individual patient. Consistent with medically accepted best practices changes to treatment algorithms are made in conjunction with normal clinical exam and other data that treating physician has available. Embodiments described herein offer a new and powerful tool in this regard by making available regular IVC diameter or volume measurements without requiring a patient to be in a clinical setting and, potentially, providing continuous information on IVC volume metrics in near-real time.

With more and more accurate data on IVC volume metrics available to the healthcare provider based on systems described herein, more refined treatment algorithms may be devised. Such algorithms also may include a significant home-care component that was not previously possible. Table II below sets forth an alternative treatment algorithm in the form of IVC metrics to guide to patient volume status over the course of 4-5 respiratory cycles (IVC metrics employed in this algorithm include maximum and minimum diameters & IVCCI calculation (max−min)/max)×100).

TABLE II

Example of Treatment Algorithm

| | | | | |
|---|---|---|---|---|
| Measurement | IVC Ø <14 mm and IVCCI >75% | IVC Ø <21 mm and IVCCI >50% | IVC Ø <21 mm and IVCCI <50%, IVC Ø >21 mm and IVCCI >50% | IVC Ø >21 mm and IVCCI <50%, sniff or <20% quiet inspiration |
| Characterize | Low IVC Ø and high IVCCI (hypovolemic) | Normal IVC Ø and IVCCI (euvolemic) | Intermediate IVC Ø and IVCCI (intermediate) | Dilated IVC Ø, low IVCCI (hypervolemic) |
| Trend | Trending below normal | Trending within normal | Trending towards thresholds | Trending above normal |
| Assessment | Review diuretic dosing in line with the trend in IVC metric | No medication changes required based on normal metrics | Increase monitoring frequency | Consider increasing or adding diuretic |
| Intervention or no intervention | If on diuretic and other signs of hypovolemia are present omit half a diuretic dose until signal changes e.g. stop diuretic for 24-48 hrs. If not on diuretics, consider liberalization of oral fluid/salt. If on vasodilators, lower dose or discontinue if postural hypotension present | Continue current treatment regimen in line with current guideline driven standard of care, ensuring optimal dosing of one medicine | Consider up-titration of current medications in line with current guideline standard of care | Add or increase loop diuretic (e.g. 40 mg furosemide or 1 mg bumetanide) Add or increase thiazide or thiazide-like diuretic dose Consider switching from furosemide to IV loop diuretic: initiate with 20-80 mg |
| Follow up | Re-evaluate IVC trends in response to diuretic change for 2-3 days; adjust thresholds if necessary | Evaluate weekly to maintain stability | Evaluate 2x weekly to maintain stability; adjust thresholds if necessary | Re-evaluate IVC trends in response to diuretic change for 2-3 days Measure renal function within 5-10 days of diuretic change: if creatinine increase by 20% or greater, consider reducing or discontinuing diuretic or reducing the vasoactive medication |
| Additional actions | n/a | n/a | n/a | If no IVC response or continued trend elevations observed, consider vasodilator change |

Treatment algorithms as described above may allow more precise titration and management of a patient's circulating blood volume than pulmonary artery pressure. As mentioned above, a patient might have a significant increase in circulating blood volume with only minor changes in pressure. Despite the normal pressure, this added volume may have deleterious short- and long-term effects on the patient's cardiac or renal function. By directly using IVC diameter or area measurements, the patient's fluid volume could be managed more closely, without a risk of inducing hypovolemia, which could also have deleterious effects.

Figure 9:
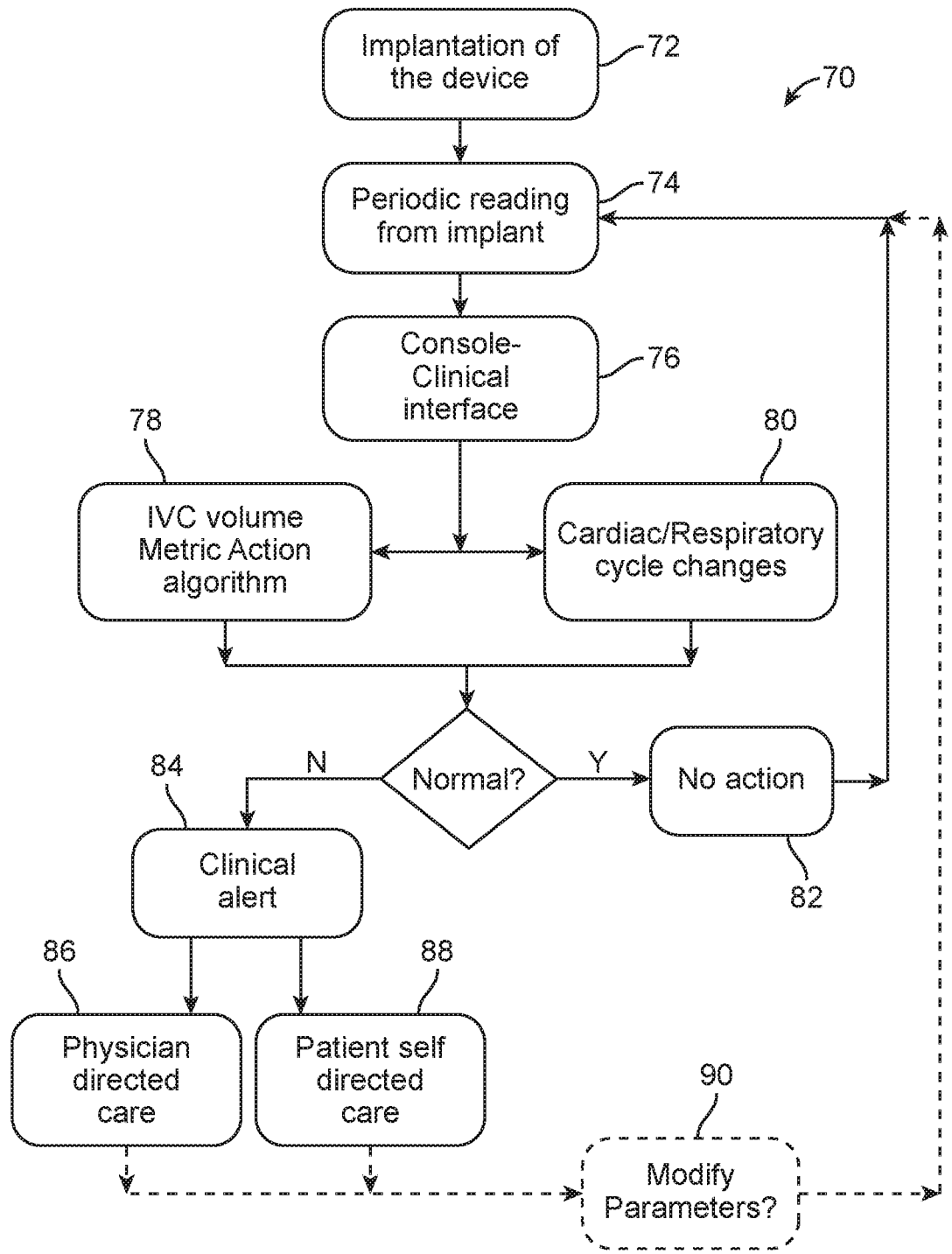
FIG. 9 illustrates an exemplary workflow utilizing a system employing an implanted IVC Volume Metric monitoring device as disclosed herein.

Utilizing embodiments described herein, it is possible to determine not only IVC metrics indicating blood volume status, but also respiration and heart rates. New clinical work flows also may be employed based on these multiple metrics to increase opportunities for improved patient outcomes. For example, as shown in FIG. 9, utilizing a system employing an implanted IVC diameter/area monitoring device, workflow 70 may include, for example, after device implantation 72, an initial detection algorithm that calls for periodic readings 74 of IVC diameter/area when the patient is at home. Such periodic readings may, for example, be taken weekly, daily or on other appropriate periods as determined by the healthcare provider based on patient parameters. In some embodiments the reading may be taken with the patient lying supine in bed and in proximity to a bedside console. Alternatively, the IVC diameter/area monitoring implant may include on-board memory, in which case it may also monitor IVC diameter or area measurements continuously or every few minutes and record the readings over the course of a day, and transmit once a day. Trend data for the selected period could be developed in this manner. Readings may be transmitted through the communications network as established to the clinical interface 76. Based on IVC metrics, i.e., blood volume as determined in the clinical interface, the treatment algorithm determines necessary interventions if any. When conditions or trends are indicated within predetermined "normal" parameters for the specific patient, no action 82 is indicated and the system resets for the next periodic reading 74. However, if a condition or trend is indicated outside of the predetermined "normal" parameters, a clinical alert 84 may be generated and suggested interventions established by the applicable treatment algorithm employed. For example, in response to clinical alert 84, the healthcare provider directed care 86 or patient self-directed care 88 may be considered as suggested interventions and one or more effected consistent with the patient treatment plan. For patients already in a clinical setting, this may include instructions to other treatment devices connected to or working with the patient (for example, as shown in FIG. 6A with system 10). Other interventions or hospitalizations may be dictated for ambulatory patients or those otherwise outside a clinical setting when the alert is generated. Particularly for patients outside a clinical setting when an initial alert is generated, through bidirectional communication, the system allows the healthcare provider to instruct the monitoring device to generate one or more confirmatory monitoring signals before treatments are added or changed, or hospitalization required. After an intervention, the system may optionally reset for the next periodic reading 74. Depending on the nature or type of the initial clinical alert 84 and interventions 86, 88, patient parameters may be modified 90 by healthcare provider input or, optionally, in some cases, automatically by the system. Modifications may include, for example, changes in frequency of prompts for periodic readings 74 or changes in treatment algorithms that may be directed by the healthcare provider 86 or patient self-directed 88.

Further exemplary embodiments may include patient fluid management methods comprising steps such as measuring the diameter of the IVC in a patient, calculation of IVC collapsibility index and/or estimating patient blood volume based on IVC collapsibility, applying a treatment to the patient to effect a change in patient fluid level when determined fluid level is outside predetermined limits, continuously or substantially continuously monitoring IVC diameter or area measurements, such as change in IVC diameter, during said treatment and modulating said treatment in response to monitored change in the IVC diameter. With such methods, treatment modulation may be accomplished in near real-time as desired. The measurement and treatment may be directly linked and operate directly in a closed loop.

In one alternative, measurement of IVC diameter or area measurements may be performed by applying an electromagnetic signal from an external transmitter to a passive implant, and sensing the electromagnetic behavior of the passive implant in response to that signal using an external receiver. In another alternative, the measuring and monitoring may comprise positioning a monitoring device at a monitoring location within the IVC configured to detect a distance between opposed walls in the IVC or the diameter/area of the IVC at the monitoring location. Examples of suitable passive implants of this type are also disclosed in the aforementioned and incorporated PCT applications by the present Applicant.

Further alternative embodiments may involve monitoring IVC dimension variation over the respiratory and cardiac cycle, which may additionally include measurement/derivation of both breathing rate and heart rate on their own and/or in conjunction with different breathing maneuvers, or exercise. Longitudinal variation over days or weeks also may be a factor monitored. In another aspect, embodiments disclosed may include algorithms that incorporate other physiologic data, such as vascular pressures, heart rate, weight, posture, exercise status, etc. and also may use data from other implanted sensors, or other external devices.

In yet another alternative, the modulating may comprise use of multiple treatment algorithms including trend analysis and reference baselines with daily or near-daily titration of medications, diet, and other therapeutic actions. Diuretic delivery also may be added with algorithms generally applicable to patient populations, or custom algorithms based on specific patient status or physiology, for example, HFpEF vs HFrEF, renal functional status.

Other exemplary embodiments include fluid management systems comprising at least one monitoring device positioned in a patient IVC and configured to monitor IVC diameter or area measurements, such as changes in the IVC diameter, and output a signal representative of those changes. A healthcare provider device may be configured to communicate with the monitoring device in the patient IVC and determine patient treatment protocols based on the output signal and an executable treatment algorithm. Interventional devices are included providing patient treatment or therapies controlled by the healthcare provider device based on the determined treatment protocols.

A further alternative embodiment is a dialysis or ultrafiltration management method comprising continuously measuring the diameter of the IVC in a patient during dialysis or ultrafiltration, estimating patient blood volume based on measured IVC diameter, and adjusting the rate of fluid removal to continuously optimize the patient's circulating blood volume. The measurement of the diameter may track diameter variations over the respiratory and/or cardiac cycle. With such a method, a patient's circulating blood volume may be rapidly reduced to an optimal level at the beginning of the dialysis session, and then maintained at that level throughout the session as interstitial fluid migrates into the circulatory system. Further alternatives in such a method may be used to optimize the dialysis procedure so as to maximize safety, by preventing episodes of hypovolemia, effectiveness, by maximizing safe fluid removal from the interstitial space over a given time period and/or long-term patient health, by safely maintaining the patient at a lower total body fluid volume than could otherwise be maintained.

Sensor Implant Examples

Figure 10:
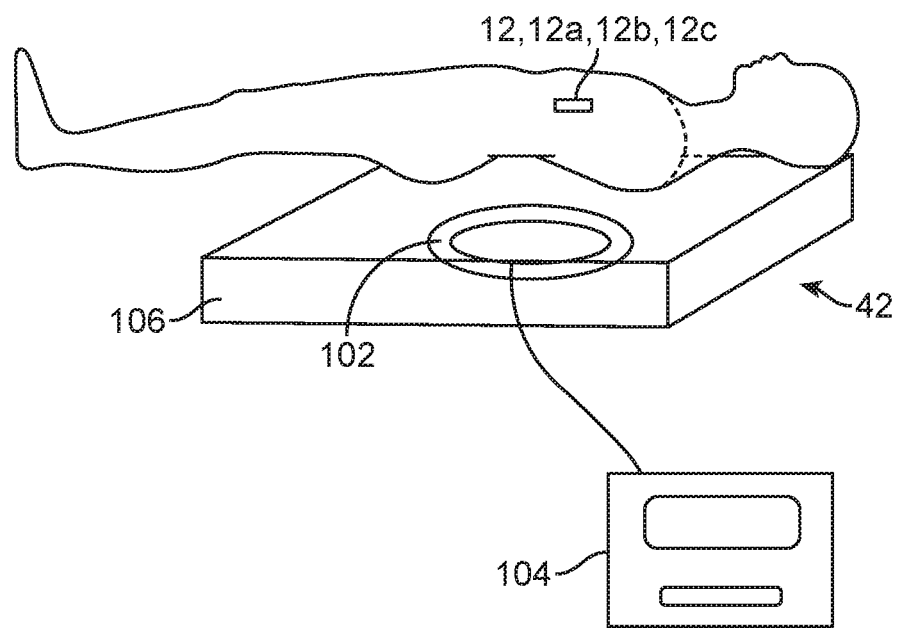
FIG. 10 schematically illustrates one embodiment of a local system for receiving signals/communicating with an implant according to embodiments disclosed herein.

Examples of sensors 12 for use with systems and methods described herein are shown in FIGS. 10, 11, 12A, 12B and 12C. As mentioned previously, systems according to the present disclosure may generally comprise an implant 12 configured for placement in a patient's IVC. Such implants 12 may in some embodiments include control and communications modules, and one or more remote systems such as processing systems, user interface/displays, data storage, etc., communicating with the control and communications modules through one or more data links, preferably remote/wireless data links. FIG. 10 shows aspects of such systems, which in some embodiments may comprise all or part of home system 42 as shown in FIG. 6B. Such a system may include an antenna/detector module 102 to communicate with and, in some embodiments, power or actuate the implant. Antenna/detector module 102 is controlled by controller 104, which may comprise a bedside console as previously described. For patient comfort, as well as repeatability in positioning, antenna/detector module 102 may be place in a pad or bed 106.

Figure 11:
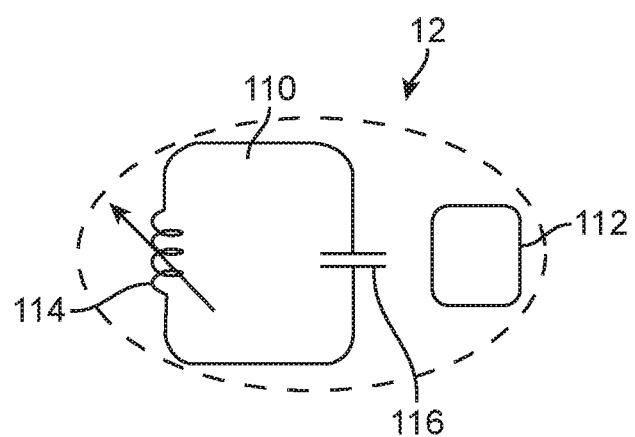
FIG. 11 presents a block diagram of one embodiment of an IVC measurement implant.

One form of implant 12 may employ a variable inductance L-C circuit 110 for performing measuring or monitoring functions described herein, as shown in FIG. 11. Implant 12 may also include means 112 for securely anchoring the implant within the IVC. Using a variable inductor 114 and known capacitance 116, L-C circuit 110 produces a resonant frequency that varies as the inductance is varied. With the implant securely fixed at a known monitoring position in the IVC, changes in shape or dimension of the IVC cause a change in configuration of the variable inductor, which in turn cause changes in the resonant frequency of the circuit. These changes in the resonant frequency can be correlated to changes in the vessel shape or dimension by the implant control and communication system. Thus, not only should the implant be securely positioned at a monitoring position, but also, at least a variable coil/inductor portion 114 of the implant may have a predetermined compliance (resilience) selected and specifically configured to permit the inductor to move with changes in the vessel wall shape or dimension while maintaining its position with minimal distortion of the natural movement of the vessel wall. Thus, in some embodiments, the variable inductor is specifically configured to change shape and inductance in proportion to a change in the vessel shape or dimension.

Variable inductor 112 is configured to be remotely energized by an electric field delivered by one or more transmit coils within antenna/detector module 102 positioned external to the patient. When energized, L-C circuit 110 produces a resonant frequency which is then detected by one or more receive coils of the antenna module. Because the resonant frequency is dependent upon the inductance of the variable inductor, changes in shape or dimension of the inductor caused by changes in shape or dimension of the vessel wall cause changes in the resonant frequency. The detected resonant frequency is then analyzed by the control and communication components of the system to determine the IVC diameter or area, or changes therein.

Turning to specific embodiments of implant 12, implant 12a, shown in FIG. 12, is an ultrasound-based device. As shown therein, 12a comprises three major components or assemblies, electronics capsule 120, anchor element 122 and anchor isolation structure 124 connecting the electronics capsule and anchor element. Electronics capsule 120 comprises a sealed housing 126 for containing control, power and other alternative functional modules as elsewhere described herein to provide a self-contained, sealed device. Capsule 120 also provides support for marker element 128, which in the case of implant 12a is a single ultrasound marker element positioned at the inferior end of the device. Such a marker element may utilize one or more ultrasound crystals to measure IVC diameter by emitting an ultrasound pulse, and then detecting the reflection of that pulse from the opposing wall of the IVC.

Electronics capsule 120 is connected to anchor element 122 at the superior end of the capsule. Anchor element 122 as depicted in this embodiment includes a single anchor wire 130 configured in a generally figure-eight or double helix shape. Alternatively, the same configuration can be provided with two or more wires. Anchor wire 130 is pinned to telescoping deployment member 132 at both its inferior end 134 and superior end 136. Telescoping deployment member 132 includes inner member 138, which is secured to electronics capsule 120, through anchor isolation structure 124 and outer member 140. Relative motion between inner member 138 and outer member 140 moves anchor wire 130 from a collapsed position to a deployed or anchoring position. Barbs 142 may be included to ensure fixation.

Various actuation mechanisms may be utilized for deploying and securing anchor element 122. In one alternative, anchor wire 130 is resilient, with shape-memory properties configured to provide a rest state in the deployed configuration. In this alternative, implant 12a may be delivered to the desired location in the IVC via a conventional guide catheter or other suitable sheath type delivery device. When position is confirmed as described below, implant 12a is ejected from the delivery catheter or sheath with anchor element 122 self-deploying upon ejection.

A further feature of implant 12a is spacing between the marker element position relative to the anchor element, provided by anchor isolation structure 124. In general, anchor element 122 is positioned sufficiently distant from the marker elements so as to not have an effect upon the IVC size or shape at or close to the location of measurement due to the anchoring force imparted to the IVC wall. Anchor isolation structure 124 facilitates the desired positioning, which may be distance approximately 1 to 4 times the IVC diameter from the measurement location.

FIGS. 12B and 12C illustrate further details of resonant circuit-based implants 12b and 12c, respectively. Implant 12b may comprise a "dog-bone"-like shape with a coil portion 150 and a capacitor portion 152. Implant 12b may comprise an electrically conductive wire or bundle of wires that is wound or otherwise formed into a single continuous coil comprising multiple turns or loops having an oval or rounded rectangular shape. It may be advantageous to use "Litz" wire, which has multiple independently insulated strands of wire, for the coil, since that may enhance the inductance of the implant. The coil is configured to be oriented such that the longer dimension of the rectangular loops extends longitudinally in a cranial-caudal direction within the IVC. The wire or group of wires may be wound multiple times in a continuous overlapping manner such that the rectangles each are defined by two or more parallel strands or bundles of wire about their periphery. The rectangles have central regions bounded by two or more longitudinal wires 154 forming spines 156 approximately defining a central plane running longitudinally in a cranial-caudal direction. This central region is configured to be disposed in a plane generally perpendicular to the anterior-posterior axis of the vessel, and remains relatively undeformed as the vessel collapses and expands in the anterior-posterior direction. The longitudinal elements may engage opposing walls of the vessel. At the caudal and cranial ends of the central regions of the rounded rectangles, the wire or wires form two lobes or a pair of coil ears 158 that flare outwardly away from each other and from the central plane of the implant in the anterior and posterior directions, as shown in FIG. 12B. Coil ears 158 are configured to engage opposing anterior and posterior walls of the vessel and to leave the central lumen of the vessel completely unobstructed for flow of blood as indicated by the arrows.

As the IVC changes shape, the longitudinal wires may move closer together or farther apart, and the coil ears may also move closer together or farther apart, thereby changing the inductance of the coil. The ears may be separated by about 1 cm to about 5 cm at the apex of the curved ends of the ears. An implant as adapted for an average IVC size may be about 2.5 cm to 10 cm long. It may be appreciated that as the IVC collapses in the anterior-posterior direction, the ears deform inwardly thereby changing the inductance of the coil. However, the central region of the coil remains relatively undeformed and maintains sufficient size that the inductance of the coil is high enough to produce a field sufficiently strong for external detection, as described more fully below. Capacitor portion 152 of implant 12b includes a capacitor element 160 to complete the RC circuit. Capacitor portion 152 can be located in a number of locations, such as distal to the ears, or along the spine.

FIG. 12C illustrates another alternative implant embodiment. The enlarged detail in the box of FIG. 12C represents a cross-sectional view taken as indicated. In this embodiment, implant 12c includes multiple parallel strands of wire 170 formed around a frame 172. With multiple strands of wires, the resonant circuit may be created with either the inclusion of a discrete capacitor, element or by the inherent inductance of the coils without the need for a separate capacitor as capacitance is provided between the wires 170 of the implant. Note that in the cross-sectional view of FIG. 12C, individual ends of the very fine wires are not distinctly visible due to their small size. The wires are wrapped around frame 172 in such a way to give the appearance of layers in the drawing. Exact capacitance required for the RC circuit can be achieved by tuning of the capacitance through either or a combination of discrete capacitor selection and material selection and configuration of the wires. In one alternative implant 12c, there may be relatively few wire strands, e.g. in the range of about 15 strands, with a number of loops in the range of about 20. In another alternative implant 12c, there may be relatively more wire strands, e.g., in the range of 300 forming a single loop.

Frame 172 may be formed from Nitinol, either as a shape set wire or laser cut shape. One advantage to a laser cut shape is that extra anchor features may cut along with the frame shape and collapse into the frame for delivery. When using a frame structure as shown in FIG. 12C, the frame should be non-continuous so as to not complete an electrical loop within the implant. As with the previous embodiment, coil wires may comprise fine, individually insulated wires wrapped to form a Litz wire. Factors determining inherent inductance include the number of strands and number of turns and balance of capacitance, Frequency, Q, and profile. One illustrative example of implant 12c may be configured as follows:

- 0.010" NiTi frame with 8 crowns (174 in FIG. 12C)—insulated with 0.013"×0.00025" wall PET heat-shrink/parylene
- overall approximately 25-30 mm diameter
- overall approximately 24 mm long
- 25 turns, 25 strand, 46AWG gold Litz wire
- No discrete capacitor element—capacitance inherent in configuration of implant
- PET heat-shrink insulation (0.065"×0.00025" wall)/parylene coated Insertion of devices into the circulatory system of a human or other animal is well known in the art and so is not described in significant detail herein. Those of ordinary skill in the art will understand after reading this disclosure in its entirety that implants 12 can be delivered to a desired location in the IVC using, e.g., a loading tool to load a sterile implant 12 into a sterile delivery system, which may be used to deliver the implant to the IVC via a femoral vein or other peripheral vascular access point, although other methods may be used.

Computer—Software Implementation

It is to be noted that any one or more of the aspects and embodiments described herein, such as, for example, related to communications, monitoring, control or signal processing, may be conveniently implemented using one or more machines (e.g., one or more computing devices that are utilized as a user computing device for an electronic document, one or more server devices, such as a document server, etc.) programmed according to the teachings of the present specification. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any non-transitory medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, smart watch, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
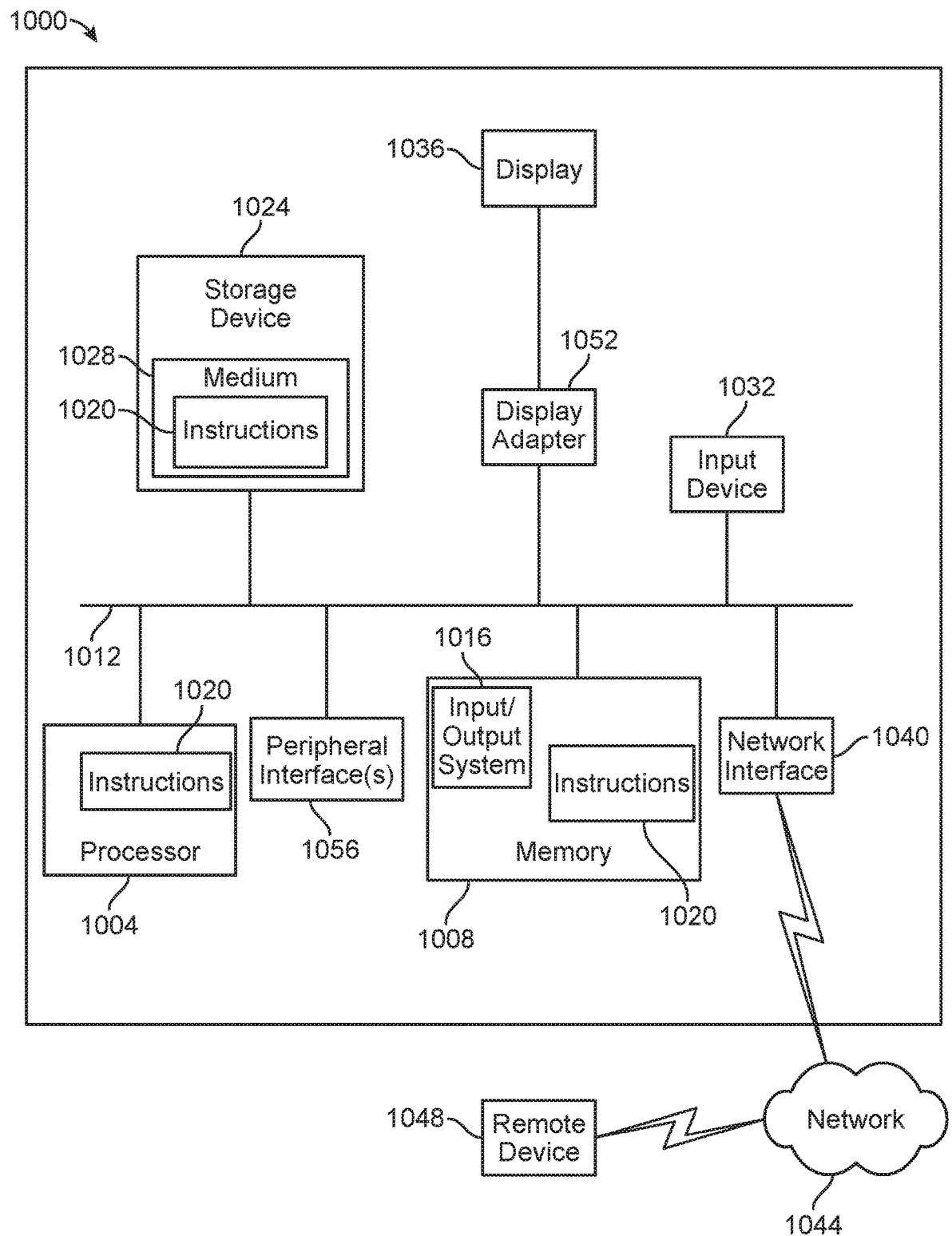
FIG. 13 a block diagram of a computing system that can be used to implement any one or more of the methodologies disclosed herein and any one or more portions thereof.

FIG. 13 shows a diagrammatic representation of one embodiment of a computing device in the exemplary form of an IVC diameter/area measuring implant control and communication system 1000 within which a set of instructions for causing an implant control and communication system, such as a waveform generator, an oscilloscope, an EFM circuit, or an implant, among other systems and devices disclosed herein, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random access memory component, a read only component, and any combinations thereof. In one example, a basic input/output system 1016 (BIOS), including basic routines that help to transfer information between elements within control and communication system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Control and communication system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with control and communication system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for control and communication system 1000. In one example, software 1020 may reside, completely or partially, within machine-readable medium 1028. In another example, software 1020 may reside, completely or partially, within processor 1004.

Control and communication system 1000 may also include an input device 1032. In one example, a user of control and communication system 1000 may enter commands and/or other information into control and communication system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to control and communication system 1000 via storage device 1024 (e.g., a removable disk drive, a flash drive, etc.) and/or network interface device 1040. A network interface device, such as network interface device 1040, may be utilized for connecting control and communication system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from control and communication system 1000 via network interface device 1040.

control and communication system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, control and communication system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

As will be appreciated by persons of ordinary skill embodiments described herein may provide a number of beneficial effects and advantages as follows:

- As a fluid status indicator: Patients can be managed with greater confidence in euvolemia—i.e. with a greater margin of safety. The physician can take enough fluid off to restore some venous capacitance to act as a buffer against sudden fluid overload causing an acute decompensation—without taking so much fluid off as to cause kidney issues (IVC Volume Metric and collapsibility (IVC CI) are both key measures of patient's fluid status, and are more sensitive/responsive than pressure).
- As a decompensation risk indicator: As IVC diameter or area measurements (e.g. diameter) increase/IVC collapsibility decreases (relative to an individual patient's baseline) it provides an earlier indicator of worsening fluid status, which in turn drives hemodynamic congestion, which drives clinical congestion (which may result in ADHF).
- As an aid to therapeutic decision making: Healthcare providers can use IVC Volume Metrics to indicate optimal diuresis point with an ability to provide longitudinal measures over a period of hours/days/weeks, helping the physician to factor in the impact of fluid redistribution (e.g., from the interstitial tissue into the intravascular space).
- As another aid to therapeutic decision making: IVC Volume Metrics assist healthcare providers in decision making as to whether to alter relative dosages of diuretics vis-à-vis vasodilators. For example, when a patient's cardiac pressure is increased, disclosed systems and methods facilitate important clinical decisions such as whether the cause is increased volume or increased vasoconstriction, whether to increase diuretics or vasodilators, whether to use IVC Volume Metrics to rule in/out increased volume as a primary cause of increased pressures, i.e., if increased volume is confirmed then diuretics may be indicated, if not then vasodilators may be indicated
- Algorithm based on inputs and output as disclosed also:
  Assesses IVC metric
  Compares daily result and trend to guideline based limits (and over time patient specific limits)
  Determines if medication modification is required
  Sends signal/message to patient and requests confirmation of medication alteration
  By exception (based on multiple times exceeding limits/trends/other trigger)
  Sends notification to managing physician
  Physician can then use system to send message to patient to modify medication and confirm change
  System may provide alarm to remind patient to take medication/take reading
  All this info is stored in the cloud server The foregoing has been a detailed description of illustrative embodiments of the disclosure. It is noted that conjunctive language such as is used herein in phrases like "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A method of managing patient body fluid volume, comprising:
   wirelessly receiving, from a sensor implanted in the patient's IVC, signals representing changes in a physical dimension of the patient's IVC;
   processing the received signals to provide IVC metrics representative of patient fluid volume state throughout an euvolemic region defined for the patient, said IVC metrics including at least one of IVC collapsibility index (CI), IVC diameter, IVC area, and a magnitude of IVC collapse over a selected period;
   comparing said IVC metrics to predetermined values associated with a plurality of patient fluid volume states to determine a current patient fluid state; and
   generating an alert signal when the determined patient fluid state meets predetermined clinical limits for the patient.

2. The method of claim 1, further comprising setting said determined clinical limits for the patient, wherein:
   said predetermined clinical limits comprise at least an indication of the patient fluid state trending towards hypovolemia, and an indication of the patient fluid state trending towards hypervolemia; and
   each of said predetermined limits falls within a euvolemic range defined for the patient.

3. The method of claim 2, wherein said setting said predetermined clinical limits comprises setting (1) a hypovolemic warning zone for said patient encompassing a portion of the defined euvolemic region at a lower end of the euvolemic region adjacent a hypovolemic region and (2) a hypervolemic warning zone for said patient encompassing a portion of the defined euvolemic region at an upper end of the euvolemic region adjacent a hypervolemic region, wherein said euvolemic range, hypovolemic range and hypervolemic range are correlated to IVC physical dimension measurements for said patient.

4. The method of claim 3, further comprising generating a prompt to initiate a fluid intervention to correct body fluid volume in response to said alert signal while patient fluid volume falls within one of said hypovolemic warning zone of the euvolemic region or said hypervolemic warning zone of the euvolemic region.

5. The method of claim 1, wherein said receiving, processing, comparing and generating are controlled by a processor executing instructions stored in a memory, and further comprising executing instructions stored in memory comprising instructions for:
defining euvolemic, hypovolemic and hypervolemic regions for said patient wherein said euvolemic range, hypovolemic range and hypervolemic range are correlated to IVC diameter or volume measurements for the patient;
determining said clinical limits by
identifying a hypovolemic warning zone for said patient encompassing a portion of the defined euvolemic region at a lower end of the euvolemic region adjacent the hypovolemic region, and
identifying a hypervolemic warning zone for said patient encompassing a portion of the defined euvolemic region at an upper end of the euvolemic region adjacent the hypervolemic region; and
generating said alert signal when measured IVC diameter or volume falls within either of the hypovolemic warning zone or hypervolemic warning zone of the defined euvolemic region before the patient fluid state reaches one of the hypovolemic region or hypervolemic region, respectively.

6. The method of claim 1, further comprising:
based on said IVC metrics identifying (1) a hypovolemic warning zone for said patient encompassing a portion of the defined euvolemic region at a lower end of the euvolemic region adjacent a hypovolemic region and (2) a hypervolemic warning zone for said patient encompassing a portion of the defined euvolemic region at an upper end of the euvolemic region adjacent a hypervolemic region, wherein said euvolemic range, hypovolemic range and hypervolemic range are correlated to IVC physical dimension measurements for said patient; and
signaling a warning state when measured IVC physical dimension falls within either of the hypovolemic warning zone or hypervolemic warning zone of the defined euvolemic region before the patient fluid state reaches one of the hypovolemic region or hypervolemic region, respectively.

7. A system for managing patient body fluid volume, comprising:
a wireless sensing device configured to be positioned within the patient IVC to measure at least one of IVC diameter or volume and generate a measurement signal representative of the sensed measurement;
a sensing device control module configured to wirelessly receive said measurement signal and output measurement data based on said measurement signal;
a processor and memory, the processor configured to receive said measurement data and execute instructions contained in the memory responsive said measurement data and to receive patient specific information, said instructions comprising
defining a euvolemic range and at least one of a hypovolemic region and a hypervolemic region for said patient wherein said euvolemic range, hypovolemic region and hypervolemic region are correlated to IVC diameter or volume measurements for the patient,
identifying at least one of
(i) a hypovolemic warning zone for said patient encompassing a portion of the defined euvolemic region at a lower end of the euvolemic region adjacent the hypovolemic region, and
(ii) a hypervolemic warning zone for said patient encompassing a portion of the defined euvolemic region at an upper end of the euvolemic region adjacent the hypervolemic region, and
generating an alert signal when measured IVC diameter or volume indicates a patient fluid state falling within either of the hypovolemic warning zone or hypervolemic warning zone of the defined euvolemic region before the patient fluid state reaches one of the hypovolemic region or hypervolemic region, respectively.

8. The system of claim 7, further comprising an interventional device configured to execute a predefined treatment algorithm for delivering a patient fluid therapy automatically in response to said alert signal.

9. The system of claim 7, wherein said alert signal includes a prompt to initiate a patient self-directed treatment or treatment change.

* * * * *